(12) United States Patent
Azhdarinia et al.

(10) Patent No.: US 11,191,778 B2
(45) Date of Patent: Dec. 7, 2021

(54) MULTIFUNCTIONAL LINKER TECHNOLOGY CONTAINING AN N4 GROUP

(71) Applicant: THE BOARD OF REGENTS OF THE UNIVERSITY OF TEXAS SYSTEM, Austin, TX (US)

(72) Inventors: Ali Azhdarinia, Houston, TX (US); Sukhen C. Ghosh, Houston, TX (US); Nathaniel L. Wilganowski, Houston, TX (US); Eva M. Sevick-Muraca, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/523,044

(22) Filed: Jul. 26, 2019

(65) Prior Publication Data

US 2020/0085862 A1  Mar. 19, 2020

Related U.S. Application Data

(63) Continuation of application No. 15/439,515, filed on Feb. 22, 2017, now Pat. No. 10,441,607.

(60) Provisional application No. 62/298,326, filed on Feb. 22, 2016.

(51) Int. Cl.
| | | |
|---|---|---|
| *A61K 47/64* | (2017.01) | |
| *A61K 33/243* | (2019.01) | |
| *A61K 33/244* | (2019.01) | |
| *A61K 33/24* | (2019.01) | |
| *A61K 39/385* | (2006.01) | |
| *A61K 39/395* | (2006.01) | |
| *C07K 16/28* | (2006.01) | |
| *A61K 33/02* | (2006.01) | |
| *A61K 49/00* | (2006.01) | |
| *A61K 38/16* | (2006.01) | |
| *A61K 39/00* | (2006.01) | |

(52) U.S. Cl.
CPC .............. *A61K 33/02* (2013.01); *A61K 33/24* (2013.01); *A61K 33/243* (2019.01); *A61K 33/244* (2019.01); *A61K 38/16* (2013.01); *A61K 39/385* (2013.01); *A61K 39/395* (2013.01); *A61K 49/0021* (2013.01); *A61K 2039/5152* (2013.01)

(58) Field of Classification Search
CPC ............ A61K 49/0021; A61K 49/0032; A61K 49/0002; A61K 49/0058; A61K 49/0056; A61K 47/6849; A61K 47/64; A61K 47/6803; A61K 51/083; A61K 51/1027; A61K 51/1093; A61K 51/088; A61K 39/395; A61K 39/385; A61K 38/16; A61K 33/24; A61K 33/02; A61K 2039/5152; A61K 49/00; A61K 33/243; A61K 33/244; C07K 16/28

See application file for complete search history.

(56) References Cited

U.S. PATENT DOCUMENTS

| | | | |
|---|---|---|---|
| 7,820,787 | B2 | 10/2010 | Meares et al. |
| 10,441,607 | B1 | 10/2019 | Azhdarinia et al. |
| 2005/0276751 | A1 | 12/2005 | Chao et al. |
| 2006/0246005 | A1 | 11/2006 | Yang et al. |
| 2007/0248537 | A1 | 10/2007 | Yang et al. |
| 2008/0035542 | A1 | 2/2008 | Mourtada et al. |
| 2008/0312431 | A1 | 12/2008 | Parker et al. |
| 2009/0004042 | A1 | 1/2009 | Matsumoto et al. |
| 2009/0087277 | A1 | 4/2009 | Azhdarinia et al. |
| 2010/0055665 | A1 | 3/2010 | Parker et al. |
| 2010/0316566 | A1 | 12/2010 | Sims-Mourtada et al. |
| 2017/0112951 | A1 | 4/2017 | Scheinberg et al. |

FOREIGN PATENT DOCUMENTS

WO  WO 2010/133851  11/2010

OTHER PUBLICATIONS

Gries et al., 1988, caplus an 1988:406552.*
Infrared Spectroscopy, 2013, http://www.ifsc.usp.br/~lavfis2/BancoApostilasImagens/ApLuminescencia/Infrared%20Spectroscop1.pdf.*
Azhdarinia et al. "Characterization of chemical, radiochemical and optical properties of a dual-labeled MMP-9 targeting peptide." *Bioorganic & medicinal chemistry* 19.12 (2011): 3769-3776.

(Continued)

*Primary Examiner* — Sun Jae Yoo
(74) *Attorney, Agent, or Firm* — Parker Highlander PLLC

(57) ABSTRACT

In some aspects, the present disclosure provides compositions comprising an N4-based MMC ligand, a cell targeting group, and a fluorophore or a therapeutic compound comprising a formula:

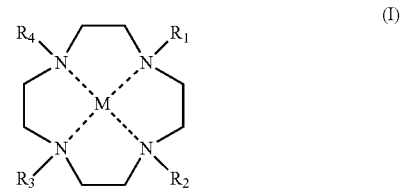

(I)

wherein the variables are as defined herein. In some embodiments, these compositions may be used in the imaging techniques or in the treatment of a disease or disorder such as cancer.

19 Claims, 7 Drawing Sheets

(56) References Cited

OTHER PUBLICATIONS

Azhdarinia et al. "Dual-labeling strategies for nuclear and fluorescence molecular imaging: a review and analysis." *Molecular imaging and biology* 14.3 (2012): 261-276.
Cheng et al., CAPlus Accession No. 1991:224663, 1991.
DeNardo et al., "Thermal dosimetry predictive of efficacy of 111In-ChL6 nanoparticle AMF-induced thermoablative therapy for human breast cancer in mice", *J. Nuclear Med.*, 48(3):437-444, 2007.
Eisenwiener et al., "A Convenient Synthesis of Novel Bifunctional Prochelators for Coupling to Bioactive Peptides for Radiometal Labelling," *Bioorg. Med. Chem. Lett.*, 10(18):2133-2135, 2000.
Ghosh et al. "Multimodal chelation platform for near-infrared fluorescence/nuclear imaging." *Journal of medicinal chemistry* 56.2 (2013): 406-416.
IR, URL: <https://www.utdallas.edu/~scortes/ochem/OChem_Lab1/recit_notes/ir_presentation.pdf>, 2012.
IR—date, 2012.
Liu et al., "Design, Synthesis and Biological Evaluation of Novel Etoposide Analogues as Cytotoxic Agents," *Chinese J. Chem.*, 24(6):785-790, 2006.
Lu et al., "Mass spectral analyses of labile DOTA-NHS and heterogeneity determination of DOTA or DM1 conjugated anti-PSMA antibody for prostate cancer therapy", *J. Pharm. Sci.*, 94(4):788-797, 2005.
Meares et al., CAPlus Accession No. 2004:825181, 2004.
Platzek et al., CAPlus Accession No. 1997:499124, 1997.
Schaeffer et al., CAPlus Accession No. 1989:469850, 1989.
Wikipedia entry for "Amino acid", URL: <https://en.wikipedia.org/wiki/Amino_acid>, 2017.
Yoo et al., "Peptidyl molecular imaging contrast agents using a new solid-phase peptide synthesis approach", *Bioconj. Chem.*, 18(3):903-911, 2007.
Yoo et al., CAPlus Accession No. 2007:245598, 2007.
Kilian, "68Ga-DOTA and analogs: Current status and future perspectives", *Rep. Practical Oncol. Radiother.*, 19:S13-S21, 2014.
Wikipedia entry for "Emission-spectrum", URL: <https://en.wikipedia.org/wiki/Emission_spectrum>, 2018.

* cited by examiner

MULTIFUNCTIONAL LINKER TECHNOLOGY CONTAINING AN N4 GROUP

This application is a continuation of U.S. patent application Ser. No. 15/439,515, filed Feb. 22, 2017, which claims the benefit of U.S. Provisional Patent Application No. 62/298,326, filed Feb. 22, 2016, the entirety of which is incorporated herein by reference.

The invention was made with government support under Grants No. U54 CA 136404-02 and R01 EB 017279 awarded by the National Institutes of Health. The government has certain rights in the invention.

BACKGROUND

1. Field of the Invention

The present disclosure relates generally to the fields of imaging agents and therapeutics. The disclosure provides, for example, compounds that are useful as imaging agents or as compounds with therapeutic payloads as well as pharmaceutical compositions and methods of use thereof.

2. Description of Related Art

Imaging-based drug design strategies are uniquely positioned to enhance how localized and metastatic tumors are treated. The development of difunctional compounds, which contain one or more imaging reporters or a combination of an imaging reporter and therapeutic compound, may be used to improve how cancer is visualized and treated. However, technical challenges in agent design such as steric interference, reduced solubility, or altered pharmacokinetics that occur from the attachment of the large molecular weight fluorescent dyes to targeting agents of similar or even smaller size have thus far limited translation of such compounds into the clinic. Since commercially available chelators are not capable of overcoming these challenges, there still remains a need for new linker complexes which may be useful as a chelating agent for clinically used radiometals, can maintain preferred targeting moiety-chelator orientation, and may be functionalization with a therapeutic payload.

SUMMARY OF THE INVENTION

In some aspects, the present disclosure provides compounds with a N4-based multimodality chelator (MMC) group, a cell targeting group, a radionuclide, a fluorophore, or a therapeutic agent. In some aspects, the present disclosure provides compounds of the formula:

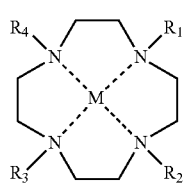

(I)

wherein:
two of $R_1$, $R_2$, $R_3$, and $R_4$ are -A-COR$_5$, wherein:
A is alkanediyl$_{(C \leq 8)}$ or substituted alkanediyl$_{(C \leq 8)}$; and
$R_5$ is hydroxy, alkoxy$_{(C \leq 8)}$, or substituted alkoxy$_{(C \leq 8)}$;
one of $R_1$, $R_2$, $R_3$, and $R_4$ is a peptide group or an antibody group;
one of $R_1$, $R_2$, $R_3$, and $R_4$ is a fluorophore group or a chemotherapeutic group; and
M is a metal atom of any oxidation state or absent;
or a pharmaceutically acceptable salt thereof. In some embodiments, the compound further defined as:

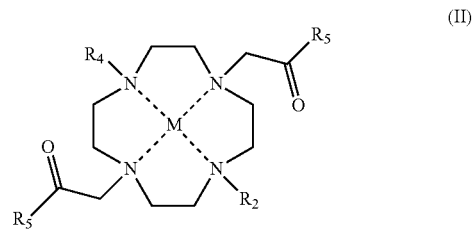

(II)

wherein:
$R_5$ is hydroxy, alkoxy$_{(C \leq 8)}$, or substituted alkoxy$_{(C \leq 8)}$;
$R_2$ or $R_4$ is a peptide group or an antibody group;
$R_2$ or $R_4$ is a fluorophore group or a chemotherapeutic group; and
M is a metal atom of any oxidation state;
or a pharmaceutically acceptable salt thereof.

In some embodiments, $R_1$, $R_2$, $R_3$, or $R_4$ is -A-COR$_5$, wherein: A is alkanediyl$_{(C \leq 8)}$ or substituted alkanediyl$_{(C \leq 8)}$; and $R_5$ is hydroxy, alkoxy$_{(C \leq 8)}$, or substituted alkoxy$_{(C \leq 8)}$. In some embodiments, A is alkanediyl$_{(C \leq 8)}$ such as —CH$_2$—. In some embodiments, $R_5$ is hydroxy. In other embodiments, $R_5$ is alkoxy$_{(C \leq 8)}$ such as methoxy or t-butyloxy.

In some embodiments, $R_2$ is a peptide. In some embodiments, the peptide comprises from 5 to 50 amino acids. In some embodiments, the peptide comprises from 7 to 30 amino acids. In some embodiments, the peptide interacts with somatostatin receptors, bombesin receptors, integrin receptors, estrogen receptors, androgen receptors, pituitary receptors, transferrin receptors, progesterone receptors, chemokine receptors, cytokine receptors, hormone receptors, and stem cell markers. In some embodiments, the interaction of the peptide with a receptor is indicative of a disease state. In some embodiments, the disease state is cancer, cardiovascular disease, neurological disorders, diabetes, vascular disease, lymphatic disease, or rheumatoid arthritis. In some embodiments, the peptide group further comprises a linker which joins the peptide to formula I. In some embodiments, the linker is further defined by the formula: —CH$_2$C(O)—.

In some embodiments, $R_2$ is an antibody group such as an antibody or antibody fragment. In some embodiments, the antibody targets CD20, CD22, CD30, CD52, HER2, VEGF, VEGFR2, EGFR, PD-1, PD-L1, EpCAM, AR, or PSMA. In some embodiments, the antibody group further comprises a linker which joins the antibody to formula I. In some embodiments, the linker comprises a thiol reactive group. In some embodiments, the linker comprises a maleimide group. In some embodiments, the linker is further defined by the formula:

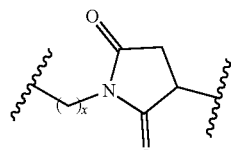

wherein: x is 1, 2, 3, 4, 5, or 6. In some embodiments, x is 3, 4, or 5.

In some embodiments, $R_4$ is a chemotherapeutic group. In some embodiments, the chemotherapeutic group is a nucleotide analog. In other embodiments, the chemotherapeutic group is selected from a topoisomerase inhibitor, mitotic inhibitor, or a nucleoside analog. The chemotherapeutic group may be selected from paclitaxel, doxorubicin, gemcitabine, topotecan, or irinotecan. In other embodiments, the chemotherapeutic group is selected from duocarmycin or duocarmycin analogs, maitansine or maitansine analogs, dolostatin or dolostatin analogs. The duocarmycin or duocarmycin analog may be selected from duocarmycin A, duocarmycin B1, duocarmycin B2, duocarmycin C1, duocarmycin C2, duocarmycin D, duocarmycin SA, CC-1065, adozelesin, bizelesin, and carzelesin. The dolostatin or dolostatin analog may be selected from monomethyl auristatin E or monomethyl auristatin F. The maitansine or maitansine analog may be selected from maitansine, mertansine, or a maytansinoid.

In some embodiments, the chemotherapeutic group further comprises a linker which joins the chemotherapeutic compound to formula I. In some embodiments, the linker is further defined by the formula: —C(O)CH$_2$—. In some embodiments, the chemotherapeutic group is 5-fluorouracil. In some embodiments, the chemotherapeutic group is further defined by the formula:

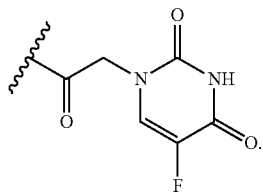 [SMILES: *C(=O)Cn1cc(F)c(=O)[nH]c1=O]

In some embodiments, $R_4$ is a fluorophore group. In some embodiments, the fluorophore group is a near infrared fluorophore. In some embodiments, the fluorophore group is a near infrared cyanine fluorophore. In some embodiments, the fluorophore group is IRDye® 800CW. In some embodiments, the fluorophore group is further defined by the formula:

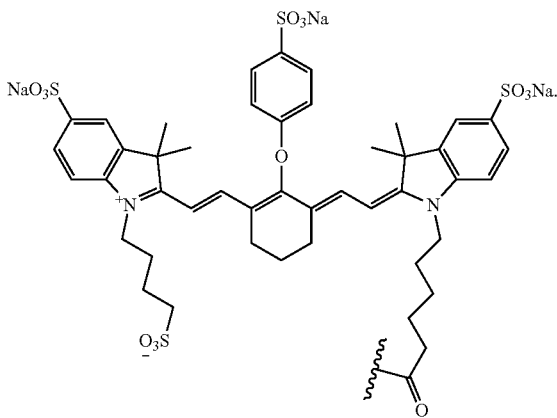

In some embodiments, the fluorophore group further comprises a linker which joins the fluorophore to formula I. In some embodiments, the linker comprises a triazole group.

In some embodiments, the triazole group is formed from the reaction of an azide and cyclooctyne. In some embodiments, the cyclooctyne is a N-substituted diarylazacyclooctyne such as N-2-aminopropionate diphenylazacyclooctyne. In some embodiments, the linker comprises an alkanediyl$_{(C \leq 8)}$ or substituted alkanediyl$_{(C \leq 8)}$ joining the triazole group and formula I. In some embodiments, the linker further comprises a carboxylic acid group. In some embodiments, the linker comprises an acylene$_{(C \leq 8)}$ or substituted acylene$_{(C \leq 8)}$ such as —C(O)(CH$_2$)$_4$—. In some embodiments, the fluorophore is further defined by the formula:

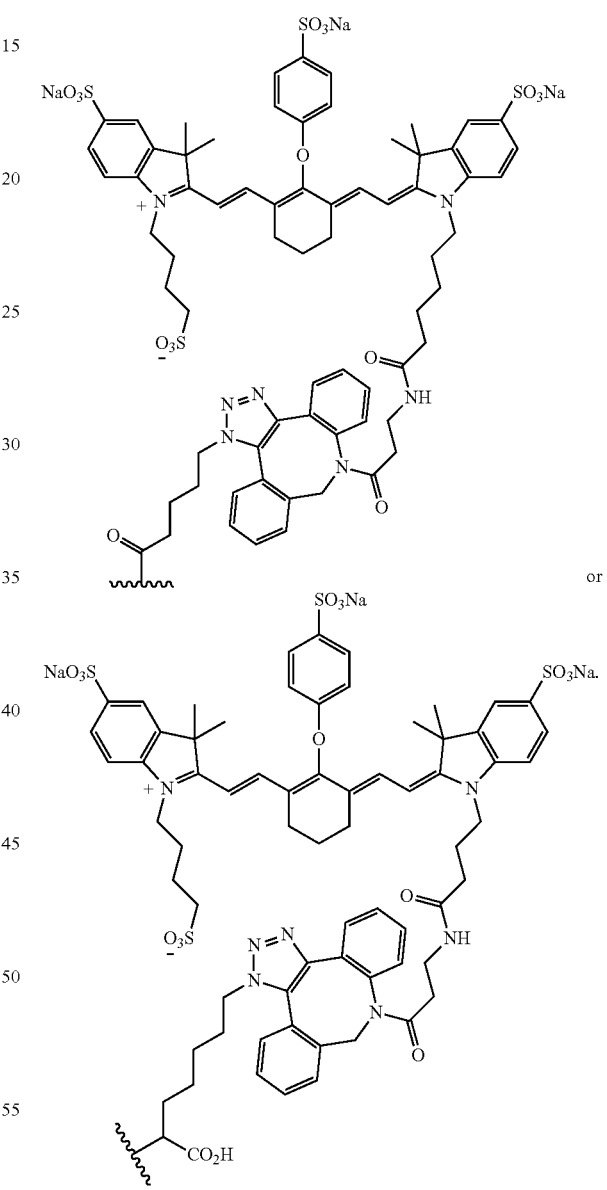

In some embodiments, M is a transition metal atom such as a radionuclide. In some embodiments, the radionuclide is $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y, $^{94m}$Tc, $^{99m}$Tc, $^{111}$In, $^{149}$Pm, $^{153}$Gd, $^{153}$Sm, $^{166}$Ho, $^{177}$Lu, $^{186}$Re, $^{188}$Re, $^{211}$At, $^{212}$Bi or $^{225}$Ac. In some embodiments, the radionuclide is $^{68}$Ga. In other embodiments, the radionuclide is $^{64}$Cu. In some embodiments, the peptide group, the antibody group, the fluorophore group, or the chemotherapeutic group is joined to the nitrogen atom of the ring system by a carbonyl group or a carbon atom which is substituted with a carboxylic acid or ester group. In some embodiments, the peptide group or the antibody group and the fluorophore group or the chemotherapeutic group is joined to the nitrogen atom of the ring system by a carbonyl group or a carbon atom which is substituted with a carboxylic acid or ester group.

In some embodiments, the compounds are further defined as:

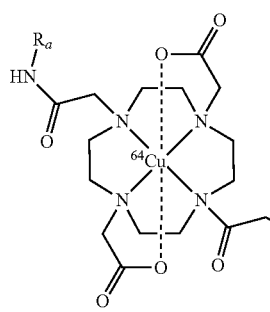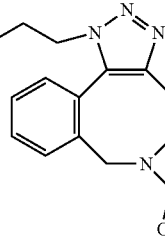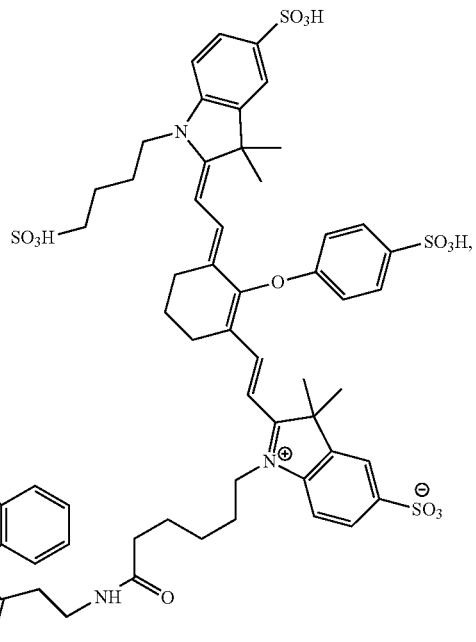

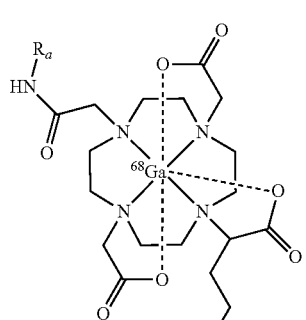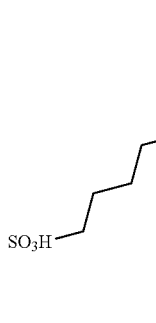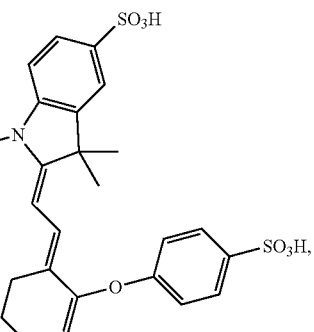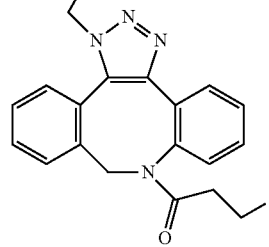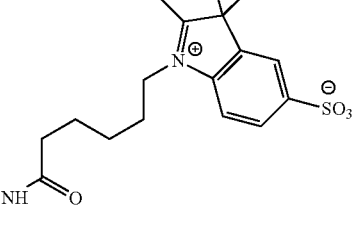

-continued
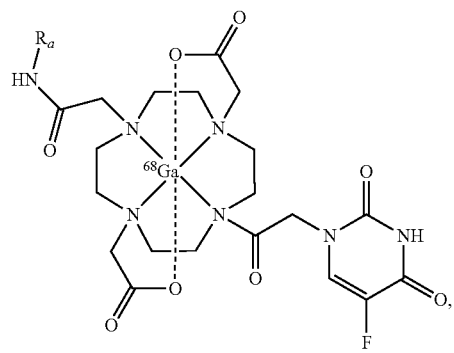
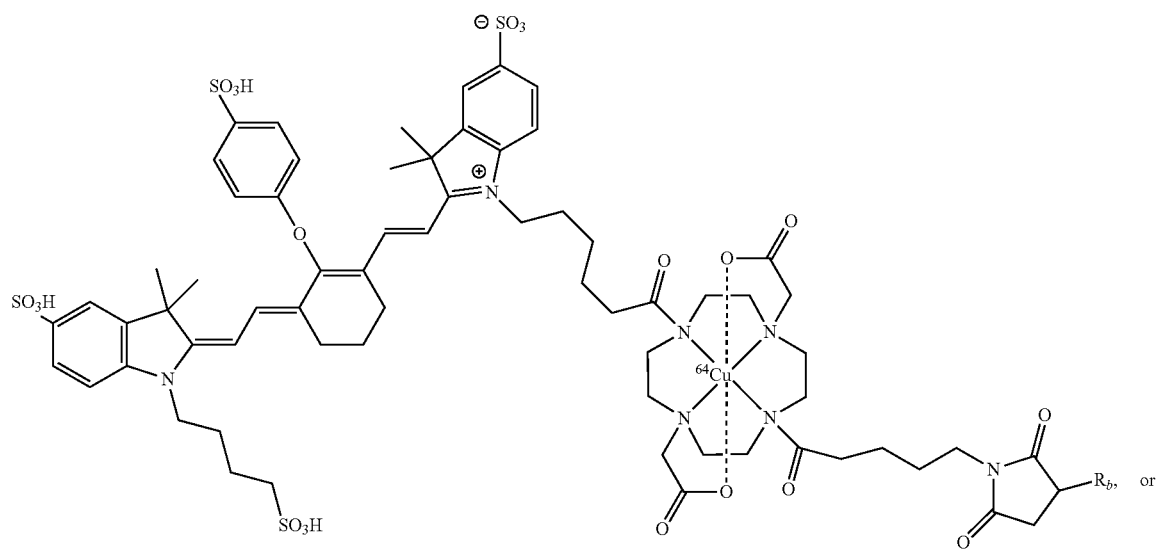
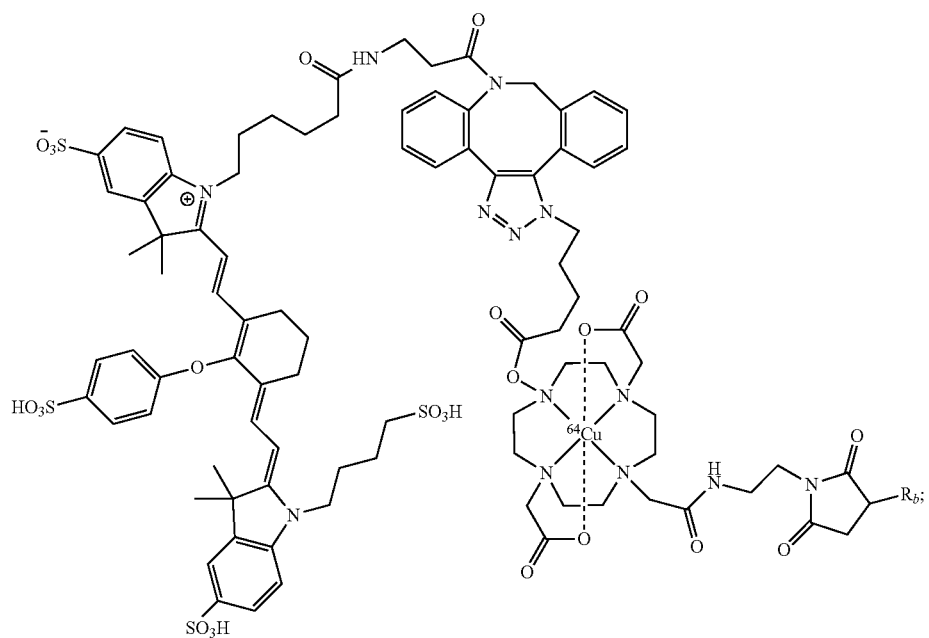

wherein:

$R_a$ is a peptide comprising from 5 amino acids to 25 amino acids; and $R_b$ is an antibody or antibody fragment;

or a pharmaceutically acceptable salt thereof.

In yet another aspect, the present disclosure provides pharmaceutical compositions comprising:

(a) a compound described herein; and (b) a pharmaceutically acceptable carrier.

In some embodiments, the compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the compositions are formulated for oral, intravenous, intradermal, intraperitoneal, or subcutaneous administration. In some embodiments, the compositions are formulated for use in imaging. In other embodiments, the compositions are formulated for use in treatment or prevention of a disease or disorder. In some embodiments, the compositions are formulated as a unit dose.

In yet another aspect, the present disclosure provides methods of delivering a compound or composition to a cell comprising contacting the cell with the compound or composition. In some embodiments, the compound or composition is selective for a particular cell type such as a tumor. In some embodiments, the methods comprise contacting the cell with a diagnostically or pharmaceutically effective amount of the compound or composition. In some embodiments, the compound or composition is useful for imaging the cell. In some embodiments, the imaging of the cell is sufficient to image a patient in vivo. In some embodiments, the patient is imaged intraoperatively. In some embodiments, contacting the cell is sufficient to assist a surgeon in the determination of tissue to be removed such as a tumor.

In some embodiments, the cell is imaged by MRI, PET, CT, SPECT, optical imaging, near-infrared fluorescence imaging, or combination imaging techniques thereof. In other embodiments, the compound or composition is useful in the treatment of a disease or disorder. In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the methods further comprise a second therapeutic agent. In some embodiments, the methods comprise contact the cell in vitro. In other embodiments, the methods comprise contact the cell in vivo. In some embodiments, the methods are sufficient to treat a disease or disorder in a patient in need thereof. In some embodiments, the patient is a mammal such as a human. In some embodiments, the methods comprise administering the compound or composition once. In other embodiments, the methods comprise administering the compound or composition two or more times.

In still yet another aspect, the present disclosure provides methods of imaging a site in a patient comprising administering to the patient a diagnostically effective amount of a compound or composition described herein and imaging the site.

In yet another aspect, the present disclosure provides methods of treating or preventing a disease or disorder in a patient comprising administering a therapeutically effective amount of the compound or composition described herein to the patient.

In still yet another aspect, the present disclosure provides kits comprising the composition described herein wherein the compound is conjugated to a peptide or antibody group which targets a disease state. In some embodiments, the kit is useful for the treatment or diagnosis of a subject. In some embodiments, the compound is further conjugated to a chemotherapeutic group or a fluorophore. In some embodiments, M is a radionuclide such as a radionuclide is selected from $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y, $^{94m}$Tc, $^{99m}$Tc, $^{111}$In, $^{149}$Pm, $^{153}$Gd, $^{153}$Sm, $^{166}$Ho, $^{177}$Lu, $^{186}$Re, $^{188}$Re, $^{211}$At, $^{212}$Bi, or $^{225}$Ac. In some embodiments, the kits further comprise an antioxidant. In some embodiments, the antioxidant is vitamin C, tocopherol, pyridoxine, thiamine, or rutin. In some embodiments, the antioxidant is vitamin C.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 5A shows retention of radiolabeling capacity following the conjugation of 5-FU to MMC-TOC. FIG. 5B shows comparable uptake of $^{68}$Ga-DOTA-TOC and $^{68}$Ga-MMC(5-FU)-

TOC in IMR-32 cells. (FIG. 5C) Blocking study in IMR-32 cells showing SSTR-mediated uptake of $^{68}$Ga-MMC(5-FU)-TOC.

FIG. 10A shows tracer accumulation in the sciatic lymph nodes in vivo by PET/CT and on resected tissues by NIRF and DsRed imaging. FIG. 10B Shows quantification of tracer uptake in resected tissues and FIG. 10C shows the corresponding tumor-to-muscle ratios (right) for immunoconjugates containing 2 and 4 MMC moieties.

DESCRIPTION OF ILLUSTRATIVE EMBODIMENTS

Figure 1:
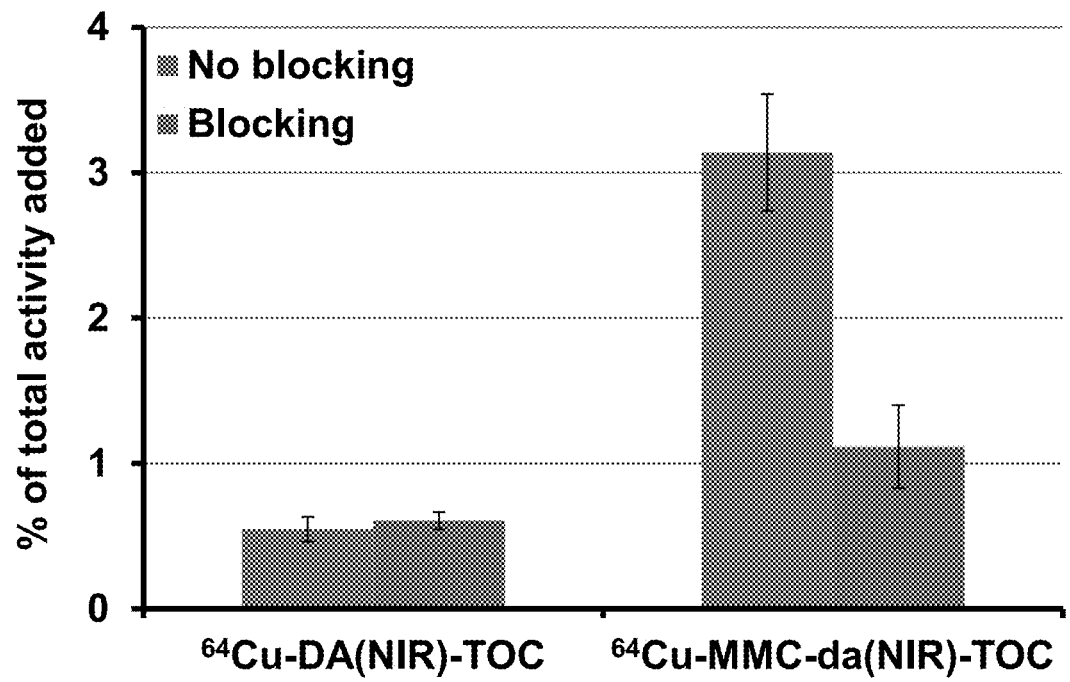
FIG. 1 shows in vitro receptor-mediated binding of $^{64}$Cu-MMC-da(NIR)-TOC and a dual-labeled conjugate produced with conventional reagents ($^{64}$Cu-DA-(NIR)-TOC) in SSTR2-expressing IMR-32 cells.

In some aspects, the present disclosure provides compositions which comprises using an N4-based MMC group as a linker between a fluorophore or chemotherapeutic compound and a cell targeting group such as a peptide or an antibody. In some embodiments, these groups can be chelated to one or more metal ions to allow for multiple forms of imaging such as PET, SPECT, and MRI or for imaging during surgery. In some embodiments, the compounds may be useful in the treatment of one or more diseases by delivering a therapeutic payload.

A. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "hydroxysulfonyl" means —S(O)$_2$OH; "sulfonamide" means —S(O)$_2$NH$_2$; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol ⹀ represents a single bond or a double bond. Thus, for example, the formula

includes

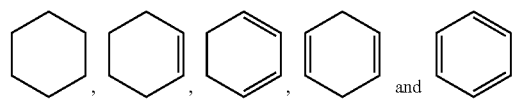

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "〰", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◢" means a single bond where the group attached to the thick end of the wedge is "out of the page." The symbol "⦀" means a single bond where the group attached to the thick end of the wedge is "into the page". The symbol "〰" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

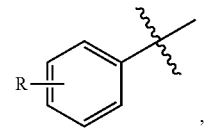

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

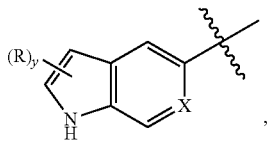

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$," or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or tBu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H-R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H-R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H-R, wherein R is alkenyl as this term is defined above. Similarly the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. The term "alkynediyl" when used without the "substituted" modifier refers to a divalent unsaturated aliphatic group, with two carbon atoms as points of attachment, a linear or branched, a linear or branched acyclic structure, no nonaromatic carbon-carbon double bond, at least one carbon-carbon triple bonds, and no atoms other than carbon and hydrogen. An "alkyne" refers to the class of compounds having the formula H-R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

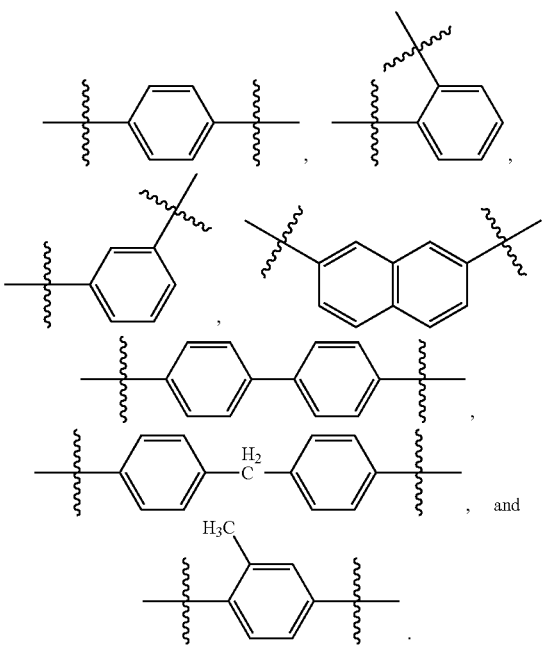

An "arene" refers to the class of compounds having the formula H-R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. The term "aralkanediyl" is the divalent group -alkanediyl-arene, in which the terms alkanediyl and arene are each used in a manner consistent with the definitions provided above. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. Heteroaryl rings may contain 1, 2, 3, or 4 ring atoms selected from nitrogen, oxygen, and sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. As used herein, a "triazole" is a chemical group with a five membered aromatic ring containing three nitrogen and two carbon atoms. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

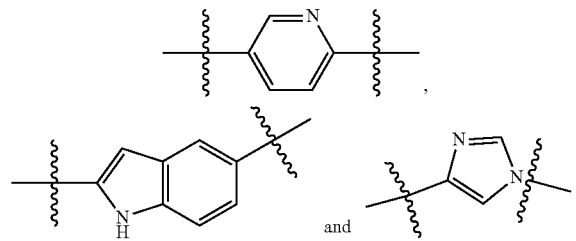

The term "N-heteroaryl" refers to a heteroaryl group with a nitrogen atom as the point of attachment. A "heteroarene" refers to the class of compounds having the formula H-R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. The term "acylene" when used without the "substituted" modifier refers to a divalent group —C(O)R—, wherein R is an alkanediyl, cycloalkanediyl, arenediyl, aralkanediyl, or heteroarenediyl as those terms are defined above. Some non-limiting examples of acylene groups including —C(O)CH$_2$CH$_2$—, —C(O)C$_6$H$_4$—, and —C(O)CH$_2$C$_6$H$_4$—. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The term "antibody" is used to described a large Y shaped protein produced by the immune system. As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, de-immunized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting. As used herein the term antibody also encompasses an antibody fragment such as a portion of an intact antibody, such as, for example, the antigen-binding or variable region of an antibody. Examples of antibody fragments include Fab, Fab', F(ab')2, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. An oxygen linked antibody is an antibody which has a chemical function group such that the linkage between the antibody and the linker or compound is joined via an oxygen atom. Similarly, a nitrogen linked antibody is an antibody which has a chemical function group such that the linkage between the antibody and the linker or compound is joined via an nitrogen atom.

The term "chemotherapeutic" is a compound, such as an antibody, a polypeptide, a nucleotide sequence, or a small molecule, which is useful for the treatment of cancer. Within this application, this term is a subset of therapeutic which is a compound (e.g. an antibody, a polypeptide, a nucleotide sequence, or a small molecule) useful for the treatment of a disease state or a disorder. In some embodiments, the chemotherapeutic is selected from alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin ω1; dynemicin, including dynemicin A; uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, or zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate;

hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; dolostatin analogs such as auristatin, auristatin E, monomethyl auristatin E (MMAE), auristatin F, monomethyl auristatin F (MMAF), or antibody drug conjugates thereof; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabine, navelbine, farnesyl-protein transferase inhibitors, transplatinum, 5-fluorouracil, vincristin, vinblastin and methotrexate and pharmaceutically acceptable salts, acids or derivatives of any of the above. In some embodiments, the chemotherapeutic is a nucleotide mimic such as 5-fluorouracil, a purine analog, gemcitabine, or 6-thioguanine.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

A "fluorophore" is a compound which emits light of a particular wavelength upon absorbance of light of a particular wavelength. In some embodiments, the fluorophore is a near infrared fluorophore which emits light from about 675 nm to about 2500 nm.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

The term "metal" refers to an atom of Groups 1-12. In some embodiments, the metal is a transition metal selected from the group 3-12 from scandium to zinc, yttrium to cadmium, and lutetium to mercury as well as lanthanoids selected from lanthanium to ytterbium and actinoids selected from actinium to neodymium inclusively.

As used herein, the term "patient" or "subject" refers to a living mammalian organism, such as a human, monkey, horse, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

A "polypeptide" or a "peptide" is a chain of amino acids linked together by peptide (or amide) bonds. In some embodiments, the amino acids may be an α-amino acid, β-amino acid, or a γ-amino acid including unnatural or non-canonical amino acids. In some embodiments, the peptide or polypeptide comprises from about 3 amino acids to about 100 amino acids. In some embodiments, the peptide comprises from about 5 amino acids to about 50 amino acids. In some aspects, the polypeptide is useful for targeting a particular receptor on the surface of a cell. Some non-limiting examples of cell targeting peptides include those described in U.S. Pat. Nos. 6,232,287; 6,528,481; 7,420,030; 7,452,964; 7,671,010; 7,781,565; 7,914,780; 7,951,362; 8,067,377; 8,252,764; 8,450,278; 8,470,528; 8,507,445; 8,562,993; 8,710,017; 8,815,231; and 8,846,859, which are all incorporated herein by reference.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

Within the context of this application, a "thiol reactive group" is a chemical functional group which undergoes a reaction with a —SH group to form a covalent bond linking the group with the thiol reactive group and the group with the —SH group. Some non-limiting examples of thiol reactive groups including maleimides, disulfides, and iodoacetamides.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the following abbreviations are used in the context of this application: TBTA, tert-butyl trichloroacetimidate; DMA, dimethylacetimide; EDCI, 1-Ethyl-3-(3-dimethylaminopropyl) carbodiimide; Pd/C, palladium charcoal; HOBt, hydroxyl benzotriazole; DIEA, N,N-Diisopropylethylamine; DMSO, dimethyl sulfoxide; NaOAc, sodium acetate; SPPS=solid phase peptide synthesis; NaOH, sodium hydroxide; $CH_2Cl_2$, dichloromethane; $K_2CO_3$, potassium carbonate; $NaNO_2$, sodium nitrite; HBr, hydrobromic acid; NaBr, sodium bromide; rt, room temperature; $CH_3CN$, acetonitrile; and $GaCl_3$, gallium chloride.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

B. COMPOUNDS AND SYNTHETIC METHODS THEREOF

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The ligands described in this disclosure may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. The ligands of this disclosure may occur as racemates and racemic mixtures, single enantiomers, diastereomeric mixtures and individual diastereomers. In some embodiments, a single diastereomer is obtained. The chiral centers of the present invention can have the S or the R configuration.

In addition, atoms making up the ligands of the present invention are intended to include all isotopic forms of such atoms. Isotopes, as used herein, include those atoms having the same atomic number but different mass numbers. The mass number of the isotope is abbreviated either as $^{13}C$ or C-13. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of the ligands may be replaced by a sulfur or selenium atom(s).

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

C. COMPOSITIONS AND METHODS OF THE PRESENT COMPOUNDS

A. Pharmaceutical Compositions, Formulations, and Routes of Administration

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The compounds of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the compounds described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compounds of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this context, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Therapeutic Methods

In particular, the compositions that may be used in treating diseases and disorders such as cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the cancer and other drugs being administered concurrently. A composition as described herein is typically administered at a dosage that induces death of cancerous cells (e.g., induces apoptosis of a cancer cell), as assayed by identifying a reduction in hematological parameters (complete blood count—CBC), or cancer cell growth or proliferation. In some embodiments, amounts of the compounds used to image a site in vivo or induce apoptosis of the cancer cells is calculated to be from about 0.01 mg to about 10,000 mg/day. In some embodiments, the amount is from about 1 mg to about 1,000 mg/day. In some embodiments, these dosing amounts may be reduced or increased based upon the biological factors of a particular patient such as increased or decreased metabolic breakdown of the drug or decreased uptake by the digestive tract if administered orally. Additionally, the compounds described herein may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In one embodiment, a second level of marker in the subject is determined at a time point later than the determination of the first level, and the two levels are compared to monitor the course of disease or the efficacy of the therapy. In certain embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

While the radionuclides that may be used for imaging include $^{68}$Ga and $^{64}$Cu, other radionuclides may also be chelated to the compounds for use as therapeutics. For example, some therapeutic radionuclides include, but, are not limited to, $^{59}$Fe, $^{67}$Ga, $^{89}$Sr, $^{90}$Y, $^{111}$In, $^{149}$Pm, $^{153}$Gd, $^{153}$Sm, $^{166}$Ho, $^{177}$Lu, $^{186}$Re, and $^{188}$Re, with $^{177}$Lu used most often. Compositions containing such therapeutic radionuclides are useful for targeted delivery of radionuclide therapy to a specific lesion in the body, such as but not limited to those associated with breast cancer, ovarian cancer, prostate cancer and head and neck cancer.

C. Kits

In some aspects, the present disclosure also contemplates that the compounds contain herein may be formulated as kits that may simplify the administration of appropriate amounts of active agent to a patient. For example, the kit may comprise a single unit dosage form of one or more of the compounds described or a pharmaceutically acceptable salt, prodrug, solvate, hydrate, or stereoisomer thereof, and/or a single unit dosage form of another agent that may be used in combination with the compounds described herein. Kits may further comprise devices that may be used to administer the active ingredients. Examples of such devices include, but are not limited to, syringes, drip bags, patches, and inhalers. Kits can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for injection USP; aqueous vehicles such as, but not limited to, Sodium Chloride injection, Ringer's injection, Dextrose injection, Dextrose and Sodium Chloride injection, and Lactated Ringer's injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. However, in some embodiments, the formulations do not contain any alcohols or other co-solvents, oils or proteins. Such kits can also contain antioxidants, such as, but, not limited to vitamin C, tocopherol, pyridoxine, thiamine, or rutin. In some embodiments, the kit is for the localization of a tumor in a subject, and in other embodiments, the kit is used to deliver a therapeutic agent such as a chemotherapeutic, radionuclide or toxin. The kit may also contain a compound that is conjugated to a targeting polypeptide group or antibody group. In other embodiments, the kit contains a compound that is conjugated to a chemotherapeutic group or a fluorophore group. In still other embodiments, the kit contains a compound that is conjugated to both a polypeptide group and a chemotherapeutic group or a fluorophore group

D. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Synthesis of a Dual-Labeled Peptide Using a Diacetate MMC Ligand

Scheme 1: Synthesis of cell targeting peptide and fluorophore containing N4-based MMC ligand.

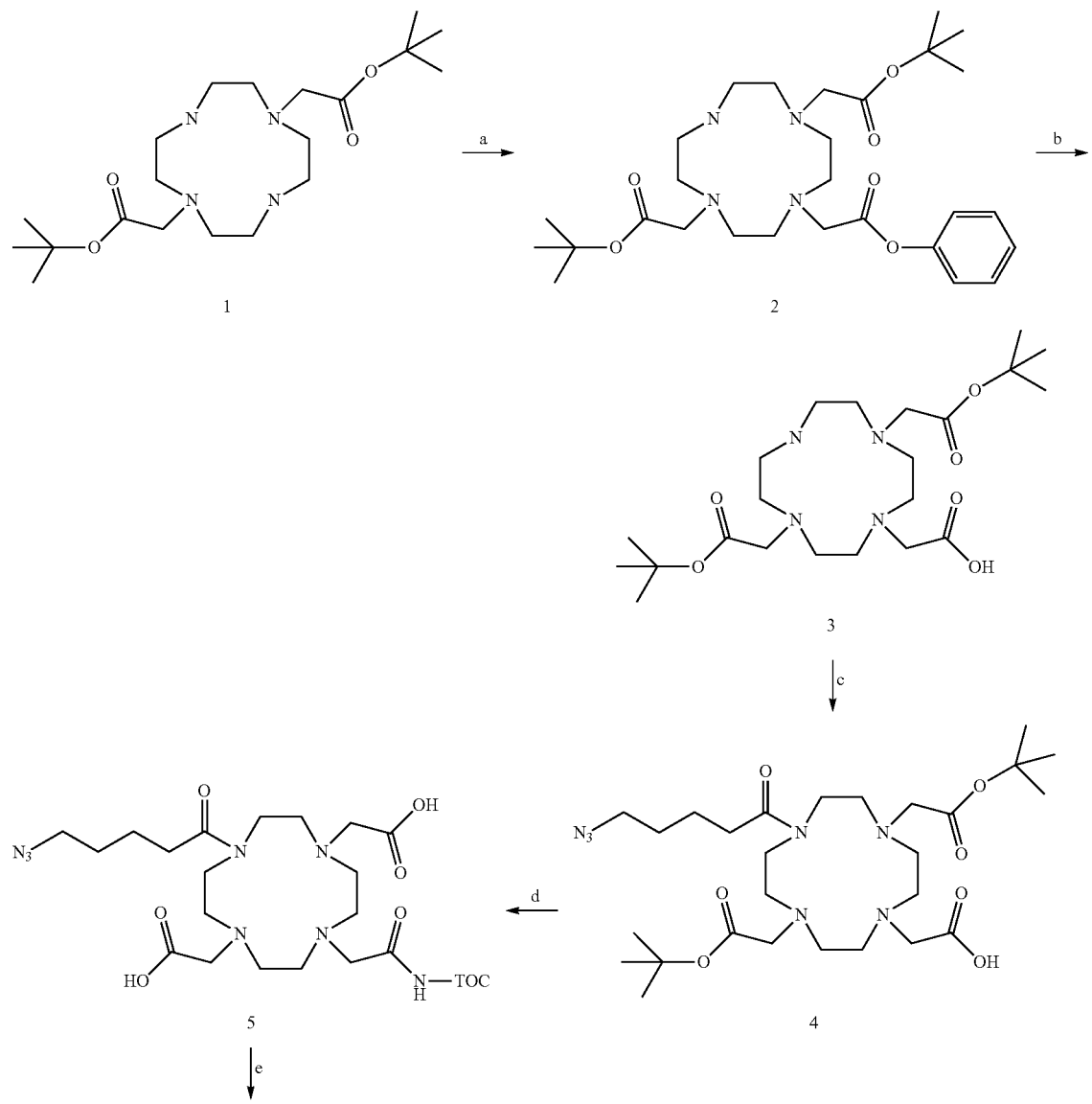

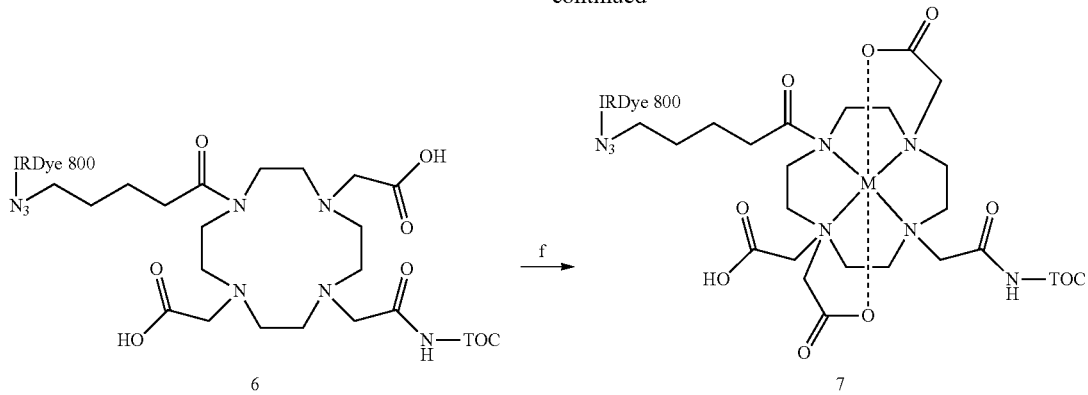

(a) Benzyl bromoacetate, K₂CO₃, CH₂Cl₂, RT, 4 h stirring; (b) Pd/C, cyclohexadiene, ethanol, 50° C., 5 h stirring; (c) 5-azido-pentanoic acid, EDC, HOBt, DIEA, CH₂Cl₂, rt overnight stirring; (d) Solid-phase peptide synthesis and deprotection; (e) DBCO-IRDye 800, DMSO/H₂O (3:1), 37° C. for 4 h, rt stirring overnight; (f) $^{64}$CuCl₂, 0.1N NaOAc, pH 6, 50° C., 1 h; M = $^{64}$Cu.

Synthesis of $^{64}$Cu-MMC-Da(NIR)-TOC

First, 0.8 equivalent of benzyl bromoacetate in 15 mL CH₂Cl₂ (anhydrous) was added dropwise into a mixture of compound 1 and anhydrous K₂CO₃ (1.5 equiv.) in 40 mL CH₂Cl₂ at room temperature. After stirring for 4 hours, the reaction mixture was filtered, evaporated, and purified by silica gel chromatography using CH₂Cl₂/MeOH (100:2) as the eluent to give compound 2 with 75% yield. Compound 2 was then hydrogenated to form compound 3 with quantitative yield for use in the next step. In order to introduce an azide functional group, compound 3 was reacted with 5-azido pentanoic acid under standard amide coupling conditions to form compound 4. Compound 4 was purified by silica-gel chromatography and the pure compound was conjugated to Tyr3-octreotide (TOC) on solid-phase using standard Fmoc chemistry and deprotection methods to form compound 5. Compound 6 was obtained by conjugating dibenzocyclooctyne (DBCO) IRDye 800 to compound 5 via click chemistry in sodium bicarbonate buffer at 37° C. for 2 hours, then 4° C. overnight. Compound 6 was purified with an ultrafiltration spin column (2,000 Da molecular weight cutoff).

For $^{64}$Cu labeling, a solution of $^{64}$CuCl₂ was diluted with 0.1 M NaOAc (pH 6) and 37-74 MBq (1-2 mCi) was added to 1-30 nmol of compound 6 in 0.1 M NaOAc (pH 6). Samples were heated at 50° C. for 1 hour and radiochemical yield was measured by radio-thin-layer chromatography (radio-TLC) using 0.1 M ammonium acetate/0.05 M EDTA (pH 6) as the mobile phase, and radiochemical purity was determined by HPLC. Compound 7 was prepared with >80% radiochemical yield and >90% radiochemical purity.

The cellular uptake of compound 7 was compared to another dual-labeled TOC agent, $^{64}$Cu-DA(NIR)-TOC, which was synthesized by sequential N-terminal functionalization of resin-bound TOC with an azide-containing amino acid and DOTA-NHS, in IMR-32 neuroblastoma cells. Agents (30 nM, 1-2 μCi) were added to vials containing 4 million cells and incubated at 4° C. for 1 hr. For blocking studies, a 200-fold excess of octreotide was added to the cells just prior to addition of the tracers. After washing twice with PBS, the cells were collected and bound radioactivity was measured by a γ counter. Cellular uptake in IMR-32 cells revealed compound 7 binding which was nearly 6-fold higher than $^{64}$Cu-DA(NIR)-TOC (FIG. 1). In addition, blocking with octreotide caused a 65% reduction in compound 7 binding but did not affect $^{64}$Cu-DA(NIR)-TOC binding.

Example 2: Synthesis of a Dual-Labeled Peptide Using a Triacetate MMC Linker

Scheme 2: Synthesis of cell targeting peptide and fluorophore containing N4-based MMC ligand with three carboxylic acids.

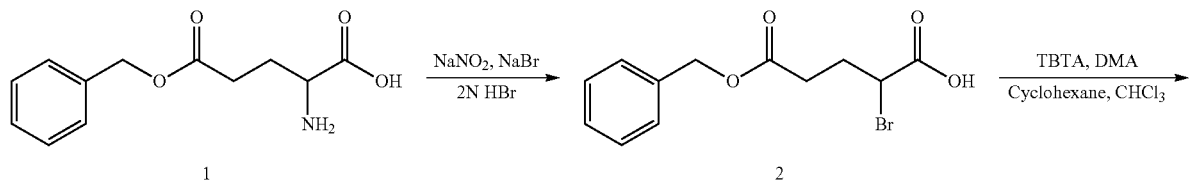

-continued
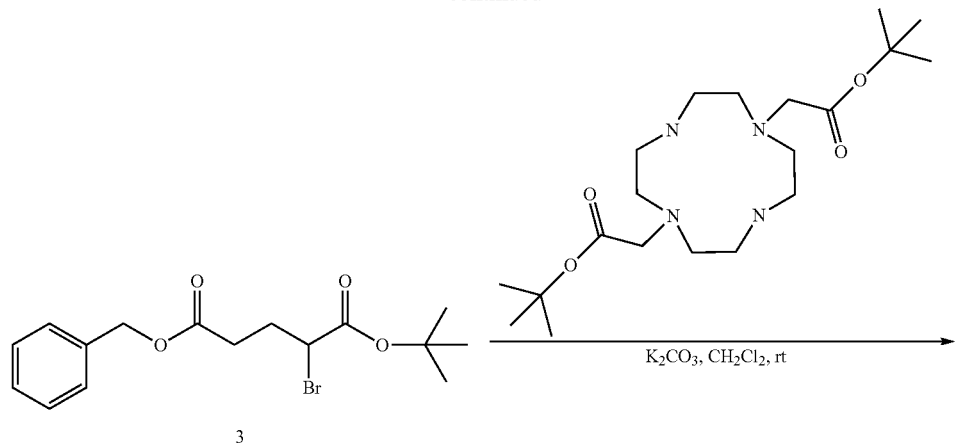
3
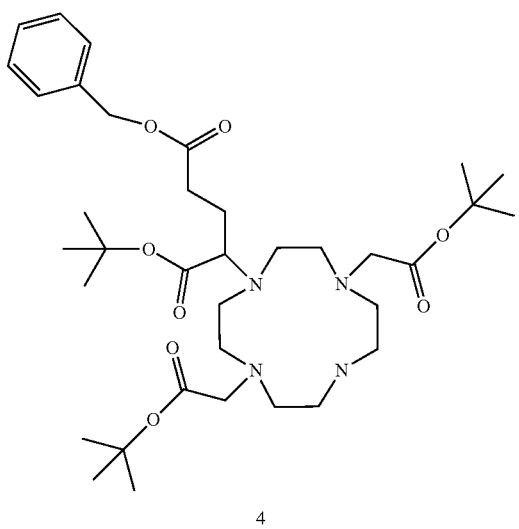
4
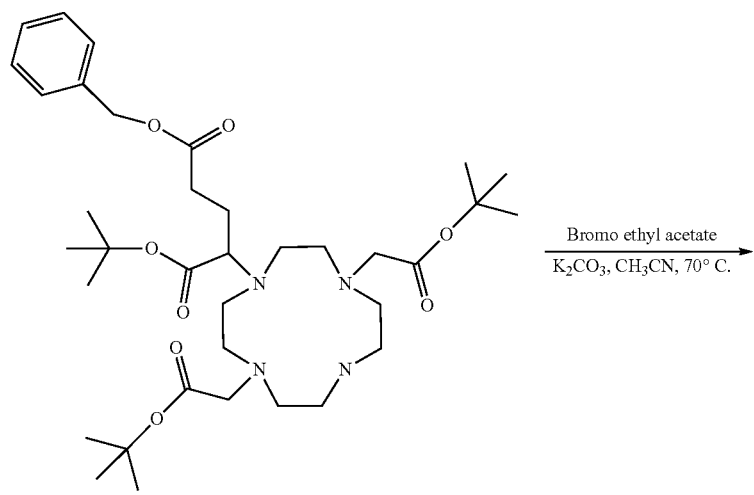
4

-continued
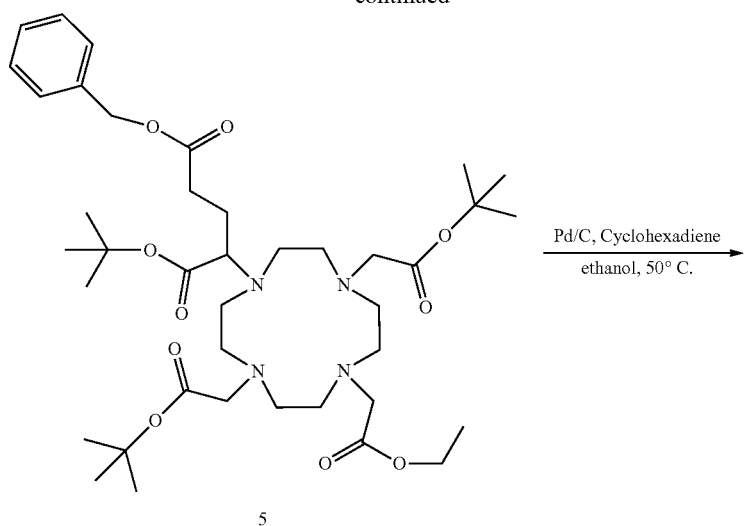
5
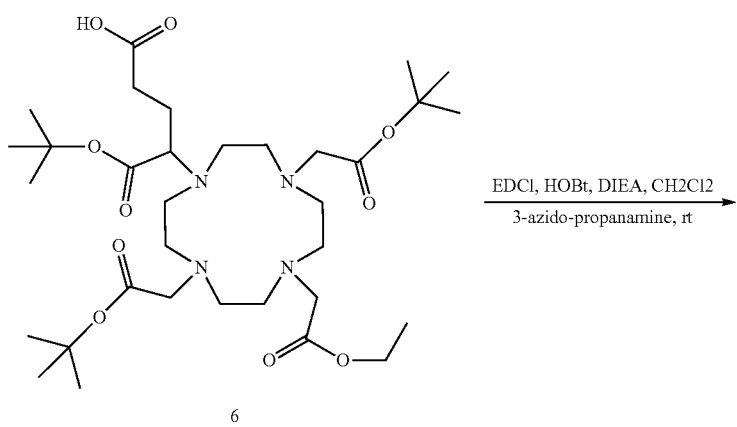
6
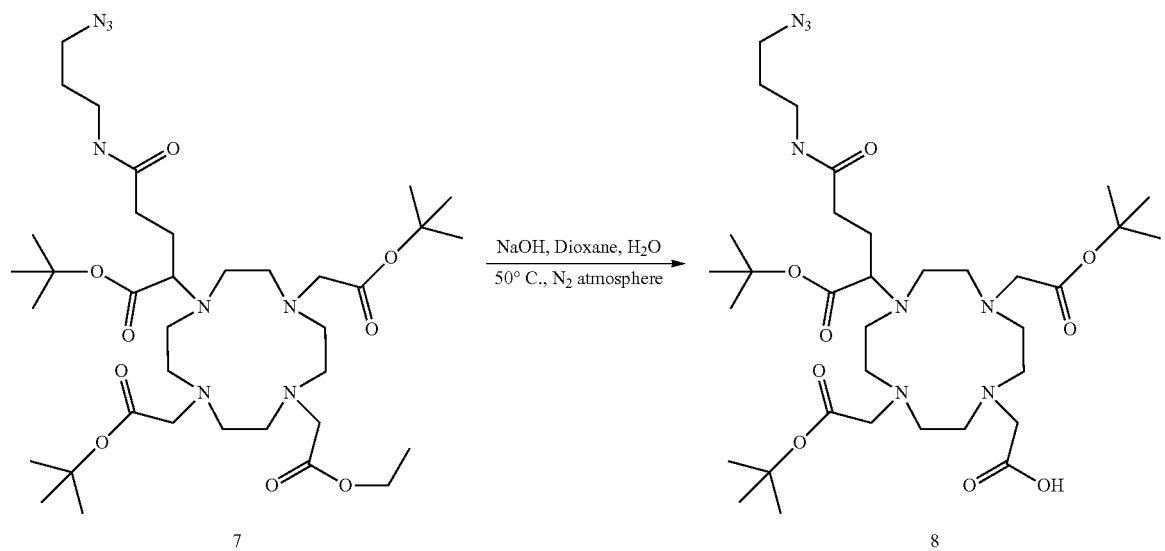
7 8

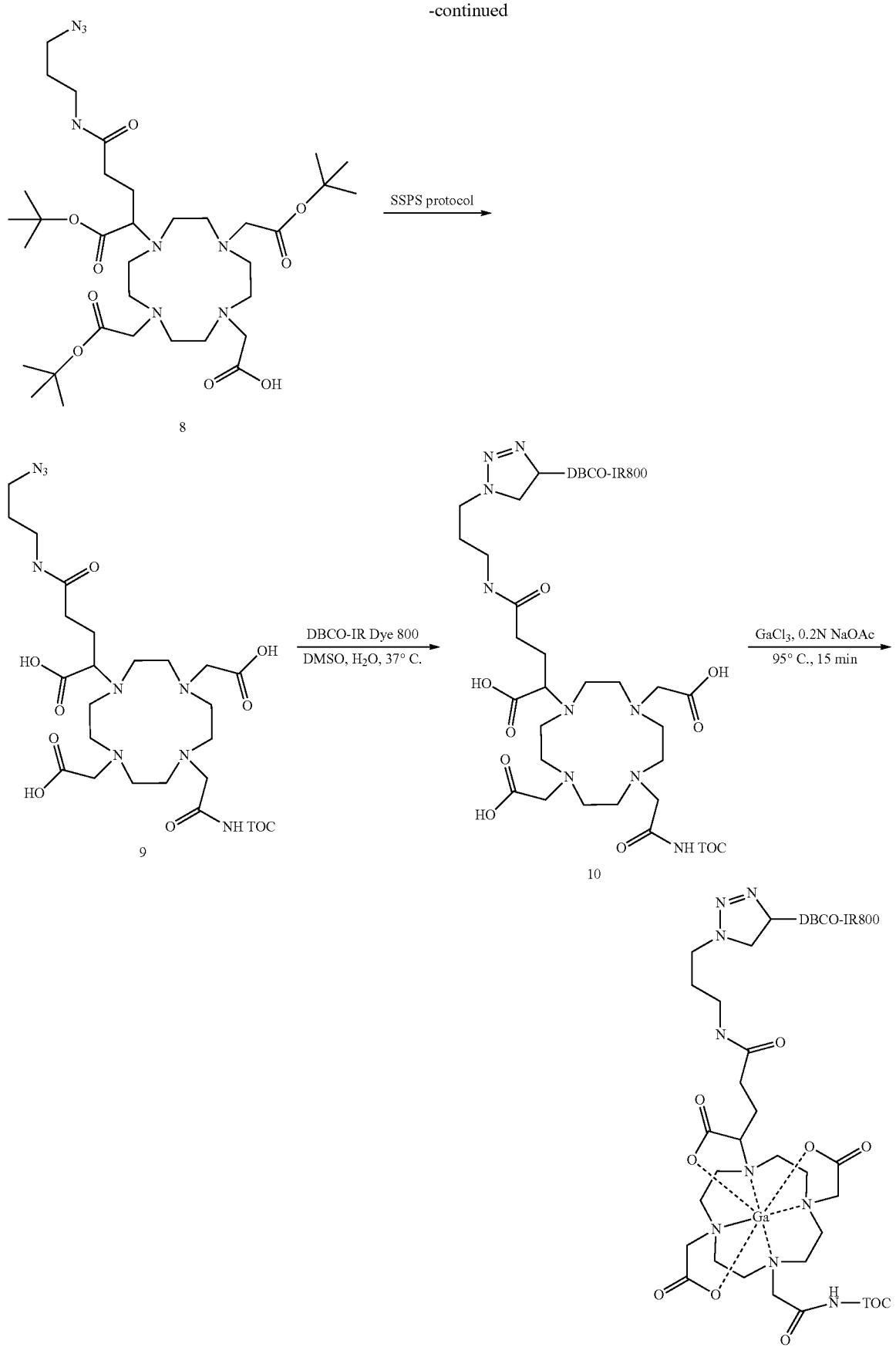

-continued

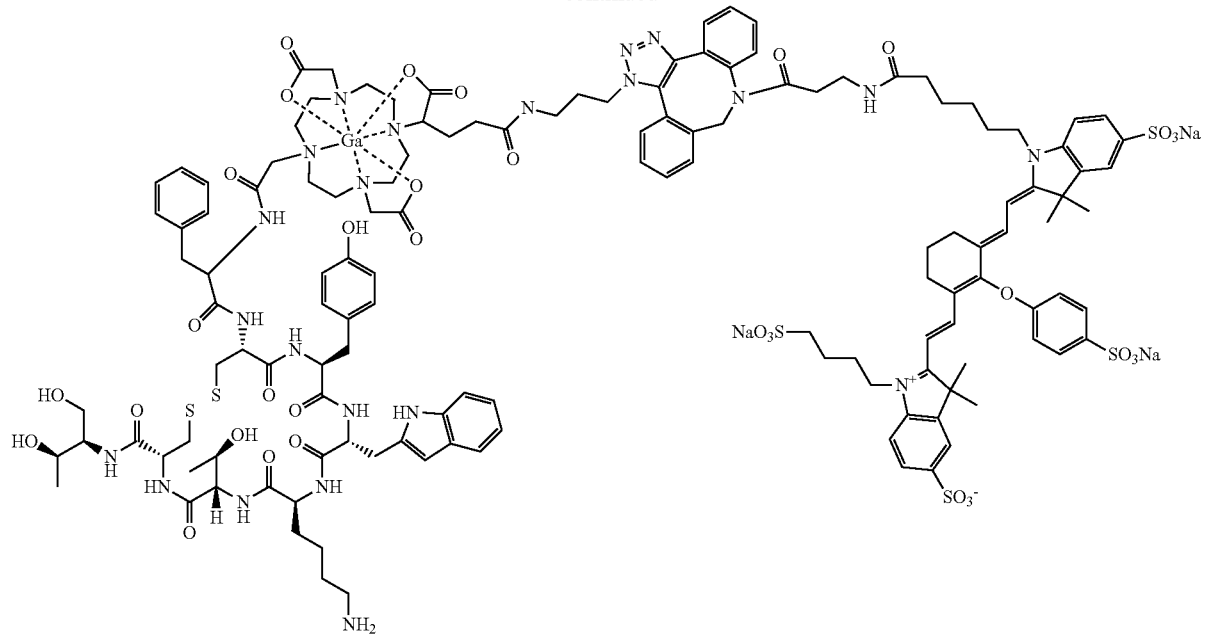

(i) NaNO₂, NaBr, 2N HBr; (ii) TBTA, cyclohexane, CHCl₃, DMA; (a) DO2A, K₂CO₃, CH₂Cl₂, RT 4 h stirring; (b) ethyl bromoacetate, K₂CO₃, CH₃CN, 70° C. for 12 h; (c) Pd/C, cyclohexadiene, ethanol, 50° C., 5 h stirring; (d) 3-azido-propanamine, EDC, HOBt, DIEA, CH₂Cl₂, rt overnight; (e) NaOH, dioxane, H₂O, 2 h at 50° C., N₂ atmosphere; (f) Solid-phase peptide synthesis and deprotection; (g) DBCO-IRDye 800, DMSO/H₂O (4:6), 37° C. for 4 h, rt stirring overnight; (h) $^{68}$GaCl₃, 0.2N NaOAc, pH 4, 95° C., 20 min.

Synthesis of $^{68}$Ga-MMC-Ta(NIR)-TOC

α-bromoglutaric acid-1-tert-butylester-5-benzylester 3 was synthesized from starting material L-glutamic acid γ-benzyl ester compound 1 according to published procedures (Eisenwiener, et al., 2000). Briefly, sodium nitrite was added dropwise to a solution of L-glutamic acid-5-benzylester and sodium bromide in aqueous 1 N hydrobromic acid cooled to 0° C. After stirring 2-3 hours, concentrated sulfuric acid was added followed by diethyl ether. The reaction mixture was extracted three times with diethyl ether. The combined organic phases were washed with brine, dried with Na₂SO₄, and concentrated. The crude product was purified by silica gel chromatography using hexane/ethyl acetate (2:1) as an eluent to collect the pure, yellow oily product 2 with high yield. Next, tert-butyltrichloroacetimidate (TBTA) in cyclohexene was added dropwise to the pure product dissolved in CHCl₃. Dimethylacetamide (DMA) was then added followed by boron trifluoride ethyl etherate as catalyst. The reaction mixture was stirred for 3 days at room temperature. The mixture was concentrated and then extracted with hexane. The crude mixture was purified by silica gel chromatography using hexane/ethyl acetate (10:1) as an eluent to collect the purified product with 65% yield. The bromo derivative 3 was then used as a starting material for the synthesis of 11.

Compound 4 was prepared by alkylating DO2A with compound 3 at room temperature in CH₂Cl₂ in the presence of K₂CO₃. Compound 4 was purified by silica-gel chromatography to carefully isolate the product from the mixture of mono and di-substituted alkylated products. The mono alkylated product 4 was reacted with ethyl bromoacetate in CH₃CN solution at 70° C. for 12 h in the presence of anhydrous K₂CO₃ to form compound 5. Compound 5 was purified from the reaction mixture with excellent yield (95%). Compound 5 underwent debenzylation by a standard hydrogenolysis procedure to form compound 6 with quantitative yield. Compound 7 was synthesized from compound 6 using EDC, HOBt and diisopropylethylamine in CH₂Cl₂ with 3-azido-propanamine. Compound 8 was synthesized from the alkaline hydrolysis of compound 7 using NaOH in a water:dioxane mixture. The reaction proceeded at 50° C. under nitrogen atmosphere for 2 h, and the product was used in the following step without further purification. Compound 8 was reacted with resin-bound TOC using standard SPPS coupling/deprotection methods to produce compound 9. Compound 10 was prepared by click chemistry by mixing compound 9 and DBCO-IRDye 800 in H₂O at 37° C. for 2 h, followed by 4 hours stirring at room temperature (85% yield). Compound 10 was purified with an ultrafiltration spin column (2000 Da molecular weight cutoff) and was characterized by HPLC and mass spectrometry.

Figures 2A, 2B:
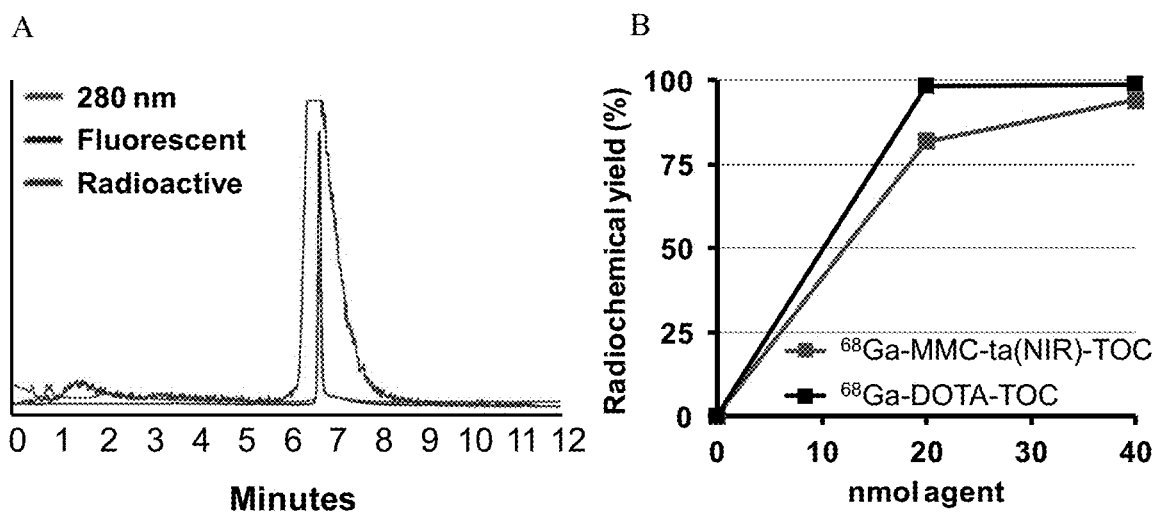
FIGS. 2A & 2B show HPLC chromatograms of corresponding UV, fluorescent, and radioactive traces (FIG. 2A) and the radiolabeling efficiency of $^{68}$Ga-MMC-ta(NIR)-TOC (FIG. 2B).
Figure 3:
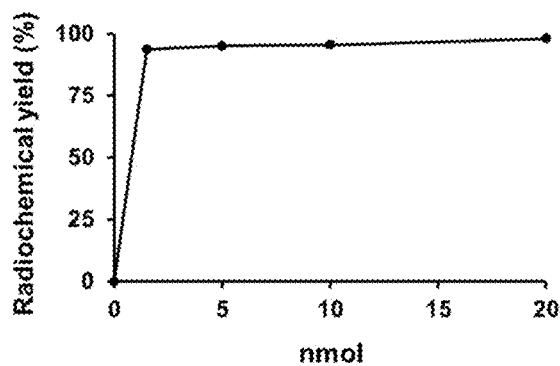
FIG. 3 shows the effects of increasing conjugate amount on radiochemical yield of $^{64}$Cu-MMC(NIR)-TOC (50° C. for 1 h, pH 6).

$^{68}$Ga labeling was performed using the cation exchange method by Zhernosekov et al. (2007). A 30 mCi $^{68}$Ge/$^{68}$Ga generator was eluted with 6 mL of 0.1 N HCl and connected to a strata-X cation exchange column for trapping of $^{68}$Ga. The column was then eluted with an acetone/HCl mixture (98:2) and the radioactivity was collected in a vial. Different peptide amounts were added to 0.2 M NaOAc buffer (pH 4) with reaction volumes ranging from 50-200 μL. Samples were heated at 95° C. for 5-20 min and purified by C-18 sep-pak columns. Radiochemical purity was determined by radio-HPLC. Compound 11 was produced with comparable radiolabeling efficiency to $^{68}$Ga-DOTA-TOC (FIG. 2). Excellent correlation between UV, fluorescent, and radioactive peaks was observed indicating successful dual labeling. Additionally, a plateau in the radiochemical yield was obtained at about 1-2 nmols as shown in FIG. 3.

Compound 10 was labeled with non-radioactive gallium according to methods established for the radiolabeled compound. Compound 10 (150 μg, 60 nmol) was mixed with an excess of non-radioactive gallium [Ga(NO$_3$)$_3$,H$_2$O] and the reaction was heated at 95° C. for 10 min. The crude mixture was purified with ultrafiltration spin columns (2,000 Da molecular weight cutoff).

Figure 4:
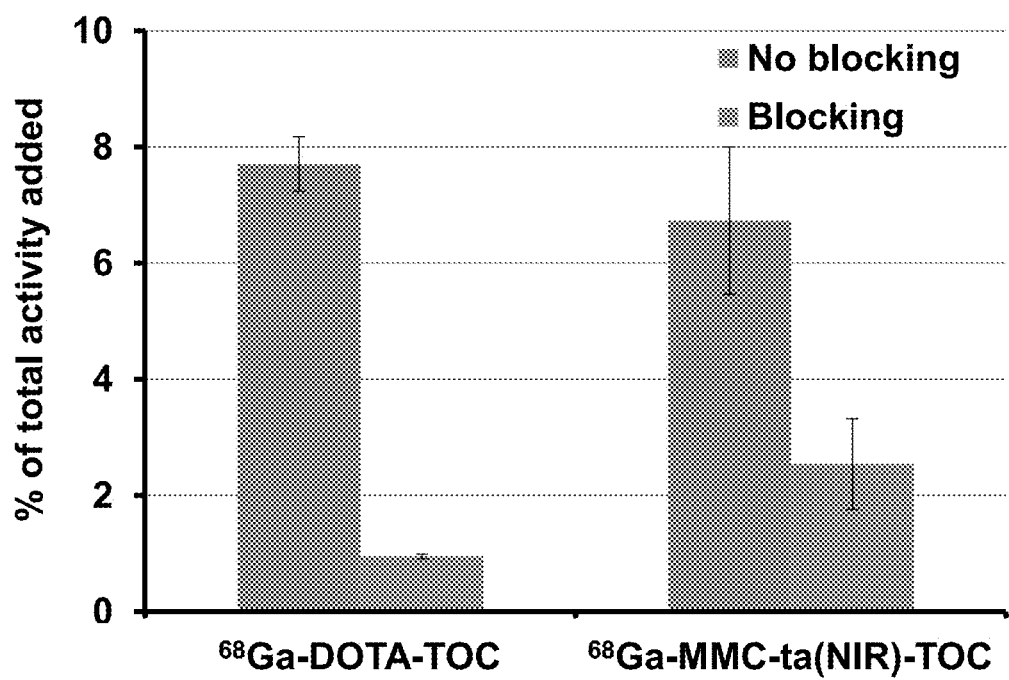
FIG. 4 shows in vitro binding of $^{68}$Ga-MMC-ta(NIR)-TOC in IMR-32 cells in the presence and absence of unlabeled octreotide.

Cellular uptake in IMR-32 cells revealed compound 11 binding which was similar to $^{68}$Ga-DOTA-TOC (FIG. 4). In addition, blocking with octreotide caused a marked reduction in compound 11 binding and indicates SSTR2 receptor specificity which is similar to $^{68}$Ga-DOTA-TOC.

Example 3: Synthesis a Chemotherapeutic Peptide-Drug Conjugate Using an MMC Ligand Scheme 3: Synthesis of cell targeting peptide and chemotherapeutic containing N4-based MMC ligand.

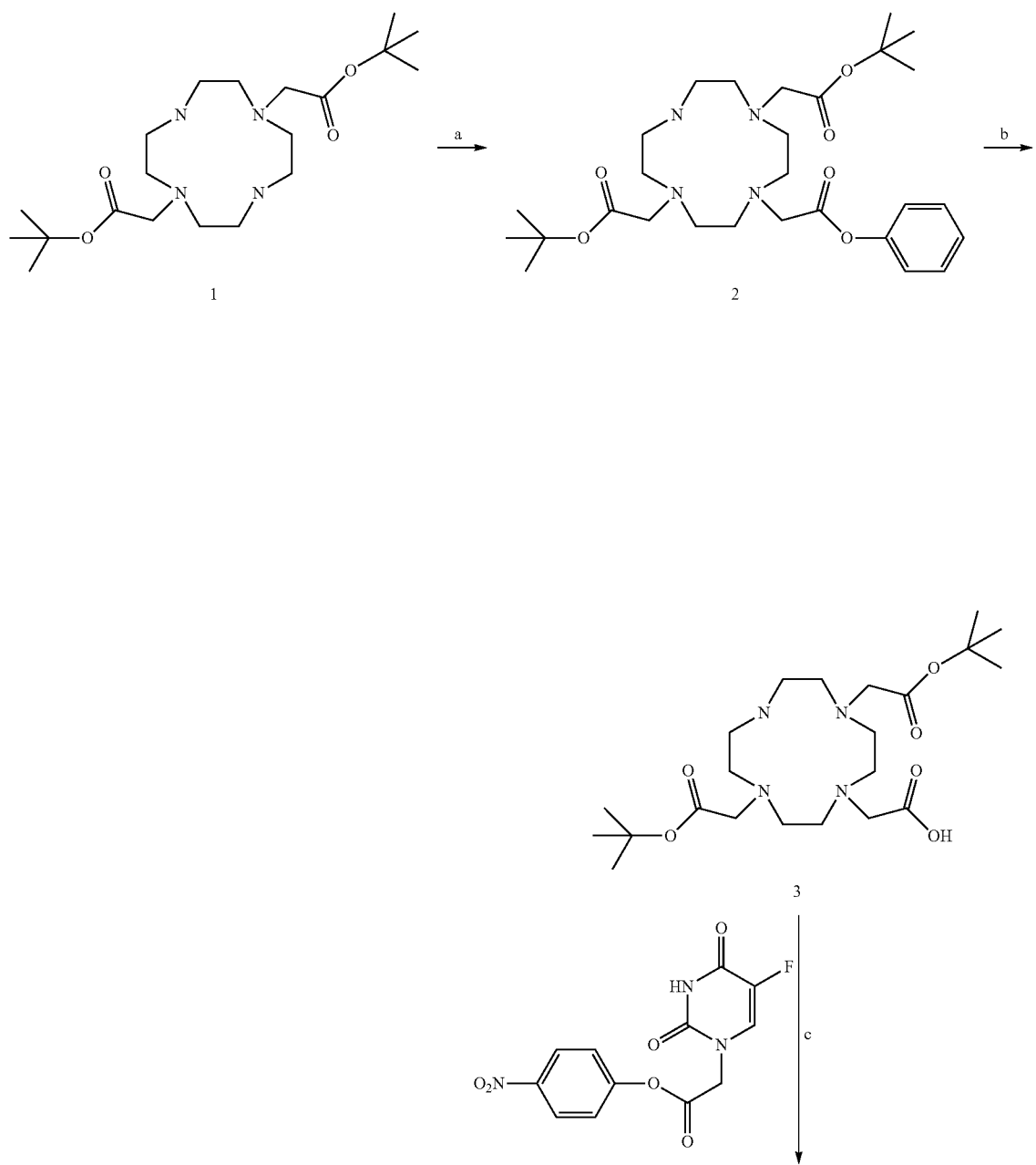

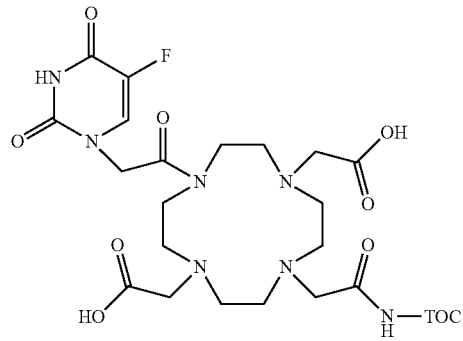
5

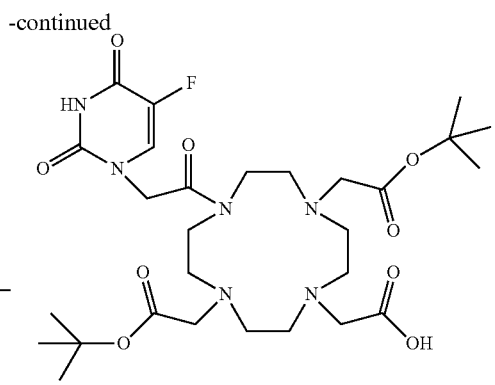
4

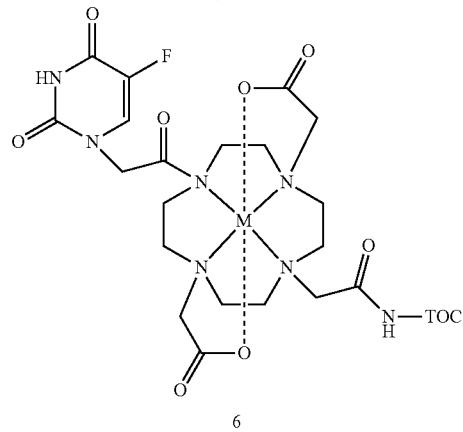
6

(a) Benzyl bromoacetate, K₂CO₃, CH₂Cl₂, rt, overnight; (b) Pd/C, cyclohexadiene, ethanol, 50° C., 5 h stirring; (c) 5-FU derivative, CH₂Cl₂ trimethylamine, rt, overnight stirring; (d) Solid-phase peptide synthesis and deprotection; (e) $^{68}$GaCl₃, 0.2N NaOAc, pH 4, 95° C., 20 min; M = $^{68}$Ga.

Synthesis of $^{68}$Ga-MMC(5-FU)-TOC

Compound 3 was synthesized as described in scheme 1. Compound c was synthesized according to a published procedure (Liu, et al., 2006). Briefly, α-chloroacetic acid was added to a solution of 5-FU in potassium hydroxide at pH 10 and stirred for 2 hours at 100° C. After cooling to room temperature, the reaction was acidified to pH 2 with HCl to form a precipitate. The precipitate was filtered, dissolved in saturated potassium hydrogen carbonate, and again acidified to pH with HCl. The precipitate was filtered and dried to produce the expected product with good yield. Next, the powder-like product was conjugated with p-nitrophenol in the presence of DCC in dimethylformamide at 0° C. for 4 hours, and then overnight at room temperature. The reaction mixture was filtered and the filtrate was evaporated to produce a white solid.

Compound 3 was conjugated with compound c in the presence of triethylamine in CH₂Cl₂ at room temperature to form compound 4. Compound 4 was purified by silica gel column chromatography using CH₂Cl₂/MeOH (100:3) as the eluent (90% yield). Compound 4 was then used for SPPS conjugation with TOC and subsequently deprotected to form compound 5. Since 5-FU is stable under conditions for SPPS, compound 4 was directly coupled to TOC on solid-phase and eliminated the need for subsequent solution-phase conjugations. This approach simplified agent production and purification, and yielded an IGDD agent. Labeling with radioactive and non-radioactive Ga were performed as described in example 2. As a result of the agent design, compound 6 was prepared with similar radiolabeling efficiency to unmodified $^{68}$Ga-MMC-TOC (FIG. 5A), suggesting that the small footprint of the 5-FU moiety has minimal steric interference on radiometal chelation.

Figures 5A, 5B, 5C:
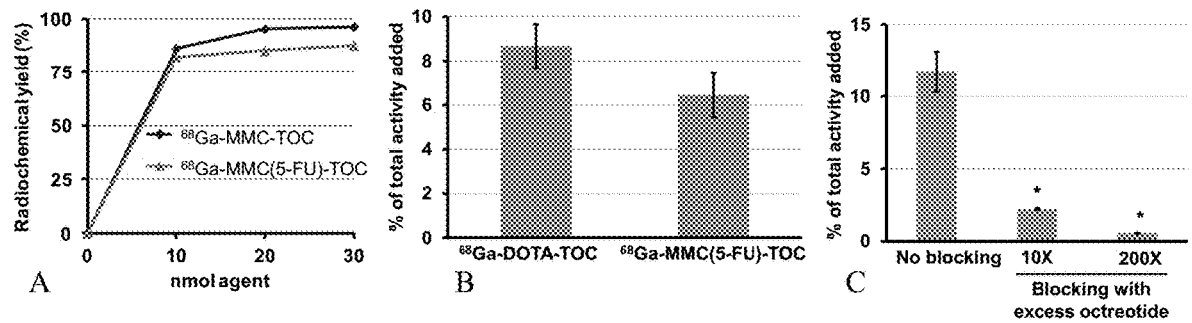
FIGS. 5A-5C show radiolabeling and in vitro characterization of a chemotherapeutic MMC-TOC conjugate.

To confirm that the addition of the therapeutic payload did not impair SSTR targeting properties of the peptide, in vitro characterization was performed and is shown in FIGS. 5B-C. Both $^{68}$Ga-MMC(5-FU)-TOC and $^{68}$Ga-DOTA-TOC exhibited good binding to IMR-32 cells, with $^{68}$Ga-DOTA-TOC having slightly higher binding compared to $^{68}$Ga-MMC(5-FU)-TOC. In a blocking study, $^{68}$Ga-MMC(5-FU)-TOC binding was reduced by 81.2% and 94.9% in the presence of a 10- and 200-fold excess of octreotide, respectively.

Figure 6:
FIG. 6 shows the PET/CT image of mice administered $^{68}$Ga-DOTA-TOC (left) and $^{68}$Ga-MMC(5-FU)-TOC (right). The arrow indicates the location of the tumor.

PET/CT images (FIG. 6) were taken of AR42J tumor-bearing mice administered $^{68}$Ga-DOTA-TOC (left) and $^{68}$Ga-MMC(5-FU)-TOC (right). As can be seen in the PET/CT images, the localization is primarily in the tumor, the kidneys, and the bladder with a higher percentage of the agent located in the kidneys for the $^{68}$Ga-DOTA-TOC agent compared to the $^{68}$Ga-MMC(5-FU)-TOC agent.

Figure 7A:
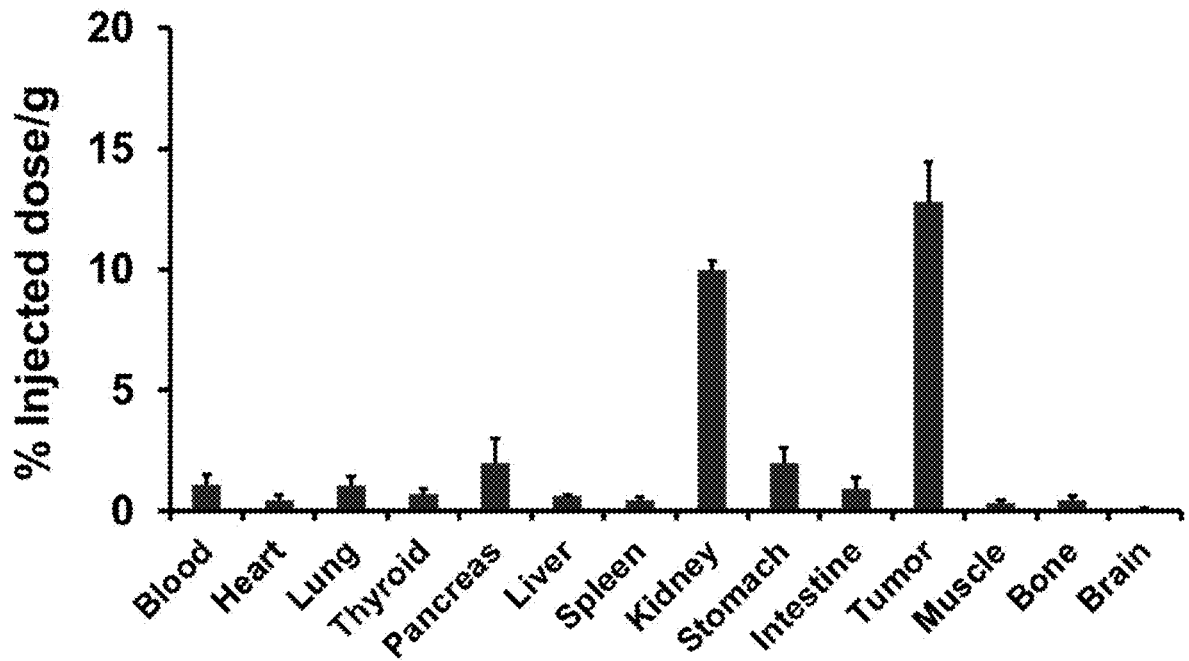
FIGS. 7A-7B. The biodistribution of the $^{68}$Ga-MMC(5-FU)-TOC agent in different tissues is shown in FIG. 7A which shows the majority of the injected dose in AR42J xenografts is located in either the tumor or kidneys with all other locations having less than 5% of the injected dose per gram. The tumor-to-tissue ratios are shown in FIG. 7B.
Figure 7B:
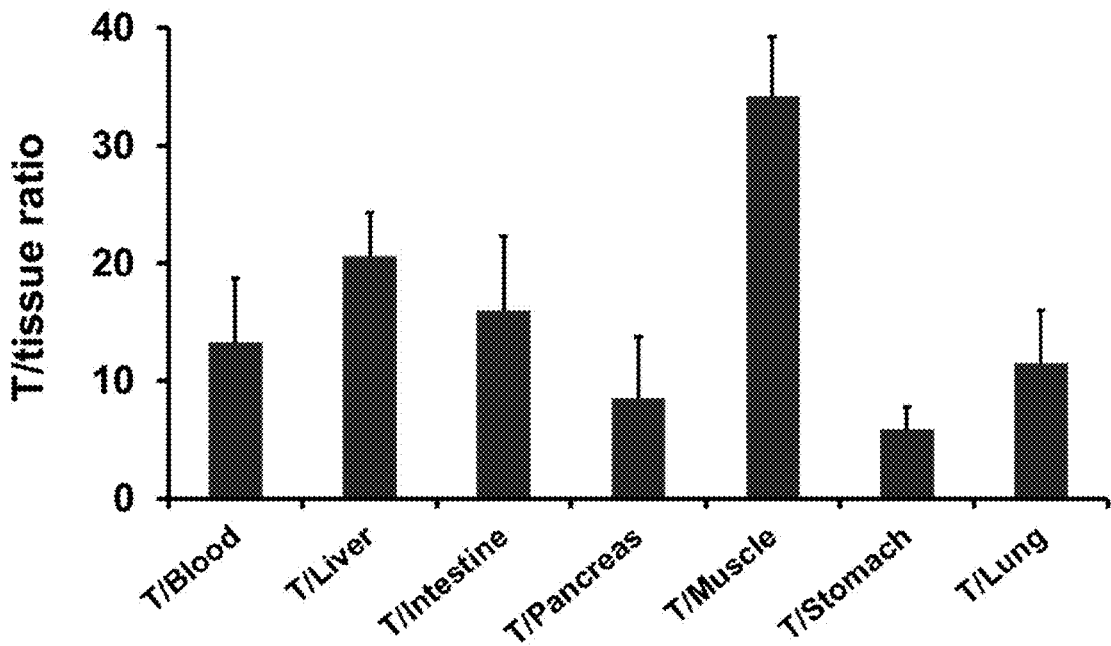

The biodistribution of the $^{68}$Ga-MMC(5-FU)-TOC agent in different tissues is shown in FIG. 7A which shows the majority of the injected dose in AR42J xenografts is located in either the tumor or kidneys with all other locations having less than 5% of the injected dose per gram. The tumor-to-tissue ratios are shown in FIG. 7B.

Example 4: Synthesis of Cell Targeting Antibody Functionalized with a Fluorophore or Chemotherapeutic-Containing MMC Ligand Synthesis of $^{64}$Cu-MMC(NIR)-mAb7

To stirring mixture of DO2A and $K_2CO_3$ in $CH_2Cl_2$, a $CH_2Cl_2$ solution of tert-butyl N-(6-bromohexyl)carbamate was slowly added at room temperature. After 4 hours, the mixture was filtered, evaporated and purified by silica gel column chromatography to produce compound 2 (65% yield). Next, compound 2 was reacted with 6-maleimido-

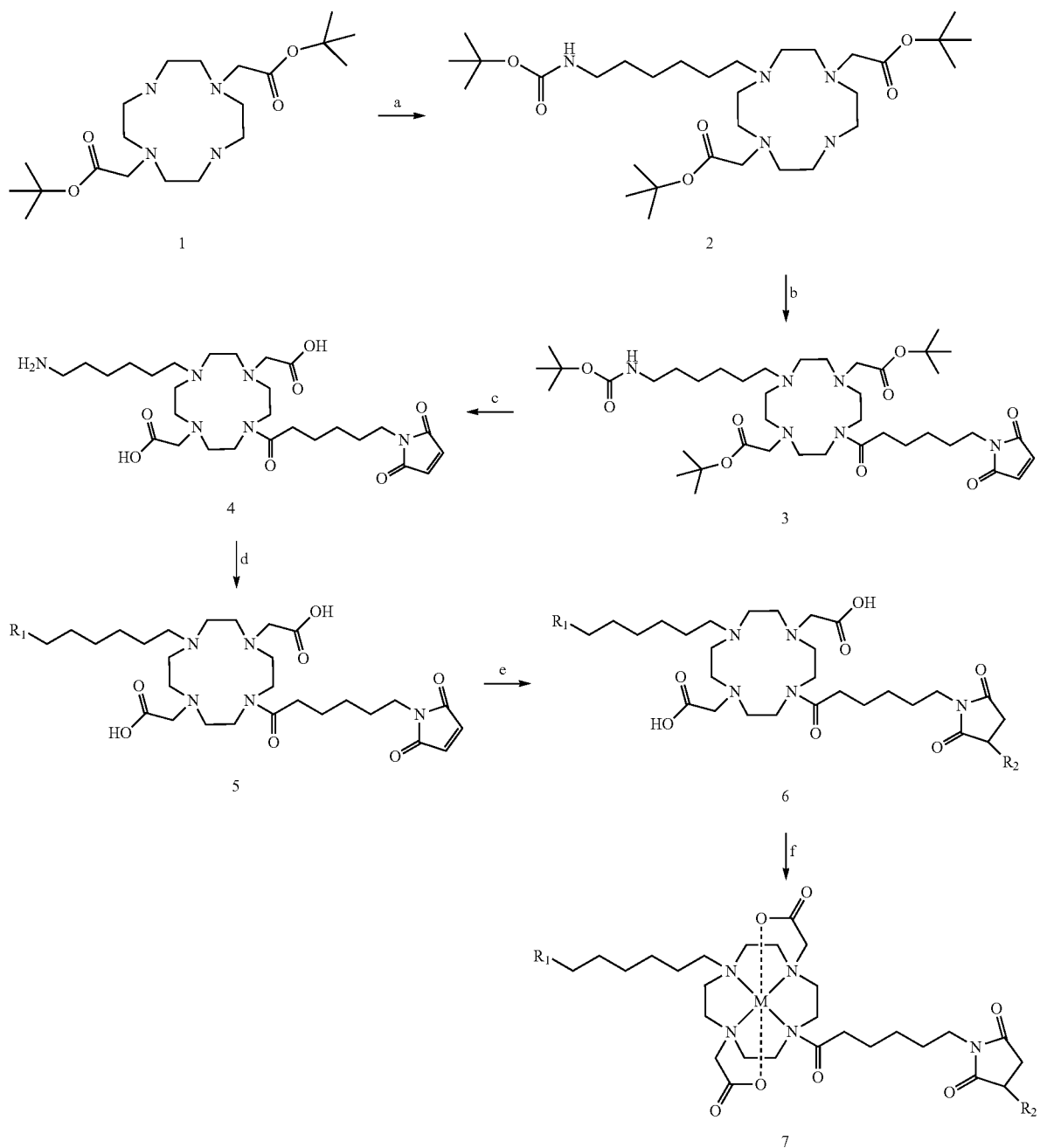

Scheme 4: Synthesis of cell targeting antibody and fluorophore or chemotherapeutic containing N4-based MMC ligand $R_1$ = NIR Dye, therapeutic compound, $R_2$ = antibody or antibody fragment-cysteine side chain, peptide-cysteine side chain. (a) tert-Butyl N-(6-bromohexyl)carbamate, $CH_2Cl_2$, $K_2CO_3$, rt, 4 h; (b) 6-maleimidohexanoic acid, DCC, HOBt, $CH_2Cl_2$, stirring 24 h, rt; (c) TFA, rt, 4 h; (d) IRDye 800 NHS ester, sodium bicarbonate buffer pH 8.5, 4° C., overnight stirring in dark; (e) antibody, phosphate buffer (0.1M pH, 7.2), 2.5 h; (f) $^{64}$CuCl$_2$, 0.1N NaOAc, pH 6, 37° C., 1 h; M = $^{64}$Cu.

hexanonic acid in the presence of HOBt, EDC, diisopropylamine and dichloromethane solution at room temperature with overnight stirring to form product 3 (95% yield). Compound 4 was prepared with quantitative yield by treating compound 3 with TFA/$CH_2Cl_2$ (1:1) for 2 hours at room temperature. Compound 4 was conjugated with IRDye 800 NHS ester (R1) in a mixture of bicarbonate buffer at 4° C. overnight. The reaction was purified by HPLC and produced compound 5. Compound 6 was synthesized by reacting compound 5 with partially reduced thiol groups on an antibody (R2) in phosphate buffer at room temperature.

To produce compound 7, a solution of $^{64}CuCl_2$ was diluted with 0.1 M NaOAc (pH 6) and 37-74 MBq (1-2 mCi) was added to 100 μg of compound 6 in 0.1 M NaOAc (pH 6). Samples were heated at 37° C. for 1 hour and radiochemical yield was measured by radio-thin-layer chromatography (radio-TLC) using 0.1 M ammonium acetate/0.05 M EDTA (pH 6) as the mobile phase, and radiochemical purity was determined by size exclusion HPLC.

Figures 8A, 8B:
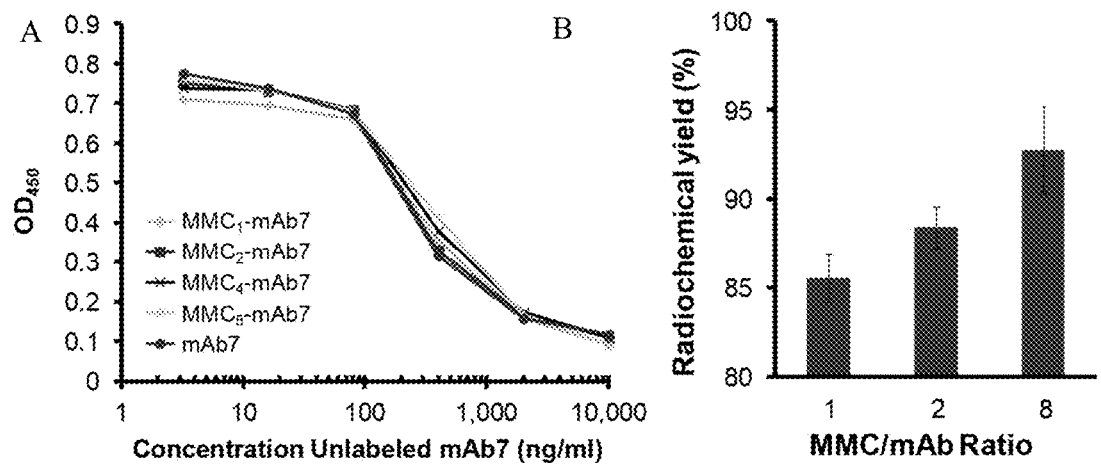
FIGS. 8A & 8B show immunoreactivity and radiolabeling of $^{64}$Cu-MMC(NIR)-mAb7 agents prepared with different MMC conjugation ratios using sulfhydryl chemistry.

Thiol linkage showed up to 8 MMC/mAb, and ELISAs showed excellent retention of binding potency regardless of the number of MMC moieties attached, demonstrating that site-specific coupling will not impair the potency of the mAb (FIG. 8A). All immunoconjugates were labeled with high radiochemical yield (>80%) and purity (>95%) (FIG. 8B).

Figures 9A, 9B:
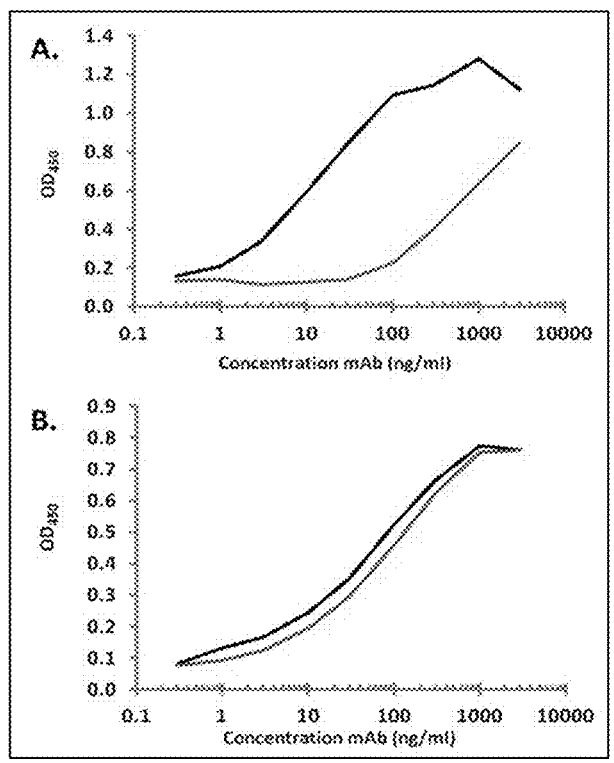
FIGS. 9A & 9B show differences in the immunoreactivity of antibodies that were dual labeled with an MMC moiety using amine coupling (gray line) (FIG. 9A) versus site-specific coupling to partially reduced thiol groups (FIG. 9B).

FIG. 9 further shows the benefit of site-specific conjugation compared to NHS methods (amide bonds) which use random lysine residues and can affect the binding region of the antibody.

Figures 10A, 10B, 10C:
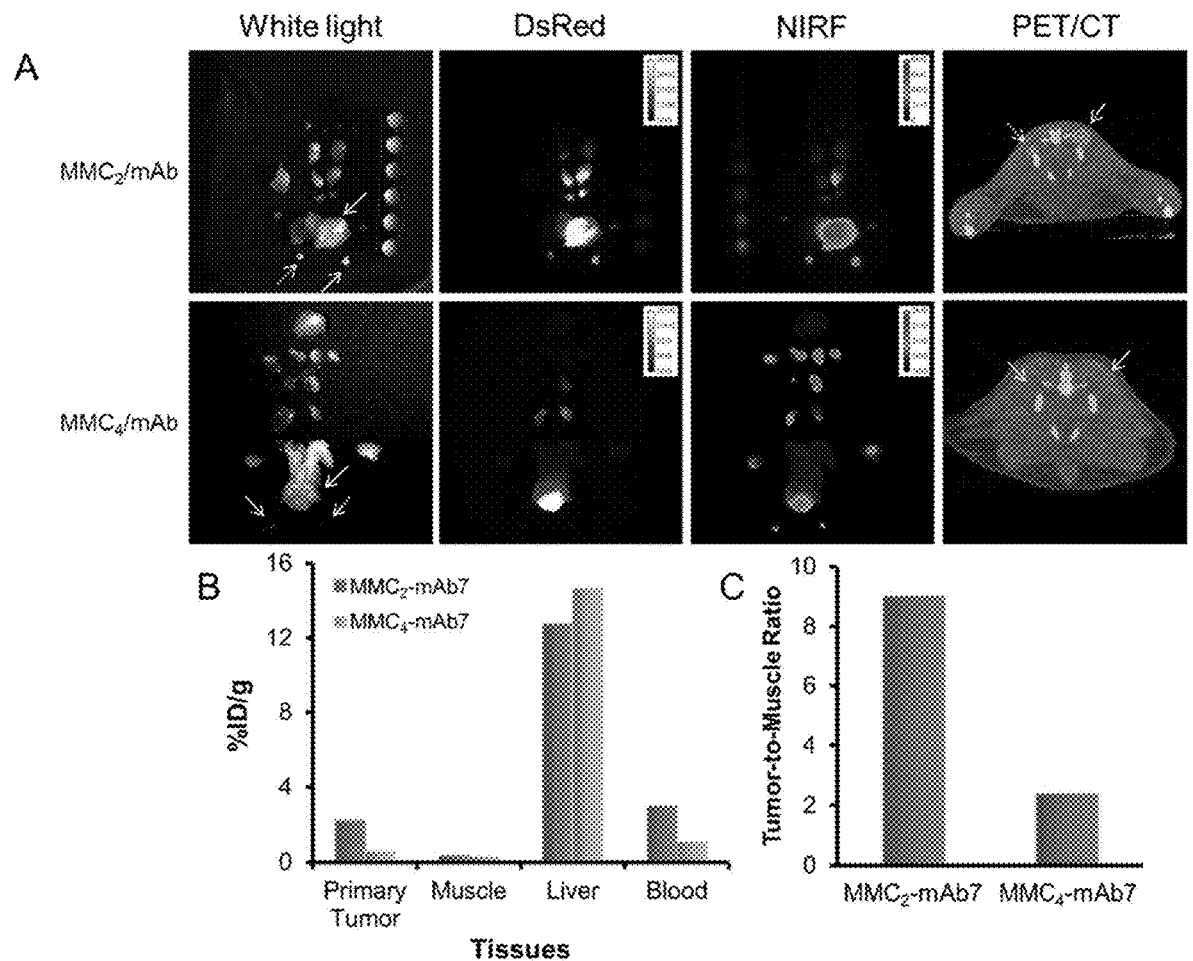
FIGS. 10A-10C show multimodal imaging with MMC immunoconjugates. (white arrows: primary tumors, grey arrows: sciatic lymph nodes.

Mice were orthotopically administered $10^6$ PC3-DsRed cells in the prostate. After 10-12 weeks, tumors were visible via DsRed imaging. Mice were injected with 7.4 MBq (200 μCi) of different batches of compound 7 possessing 2 and 4 MMC moieties per antibody. Imaging was performed 24 hours post-injection by PET/CT. Tissues were resected and underwent NIRF and DsRed imaging to determine signal localization, and gamma counting was perform to quantify tracer uptake. Images from a tumor-bearing mouse reveal sciatic lymph node uptake on PET/CT and NIRF imaging (FIG. 10A). DsRed imaging confirmed cancer positivity in these tissues and demonstrated the tumor targeting properties of compound 7 by multimodality imaging. The agent with 2 MMC moieties had the best imaging performance and significantly higher tumor uptake compared to normal (muscle) tissue as shown in FIGS. 10B & 10C.

Example 5: Synthesis of Cell Targeting Antibody Functionalized with a Fluorophore or Chemotherapeutic-Containing MMC Ligand Using Click Chemistry Scheme 5: Synthesis of cell targeting antibody and click fluorophore containing N4-based MMC ligand.

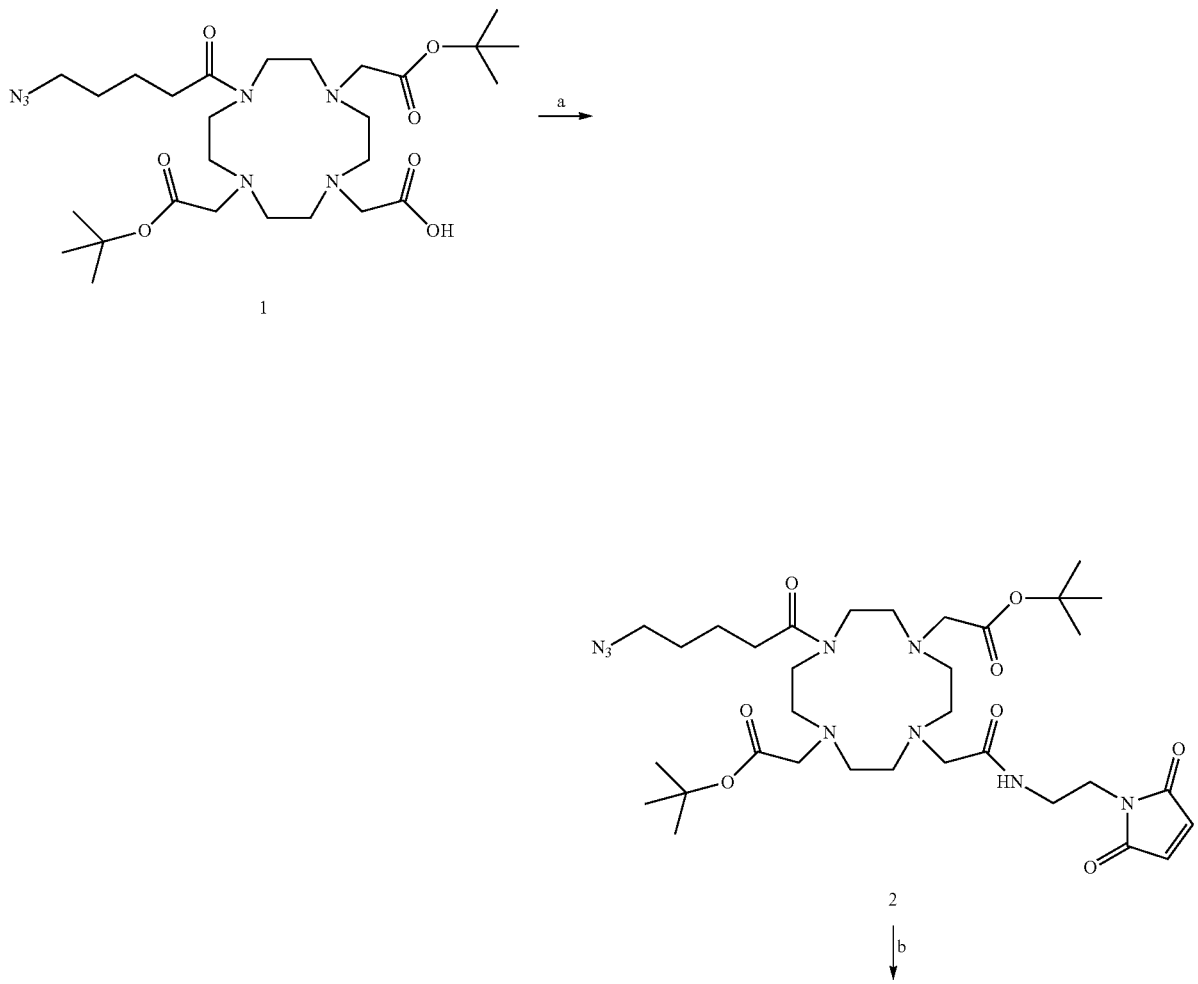

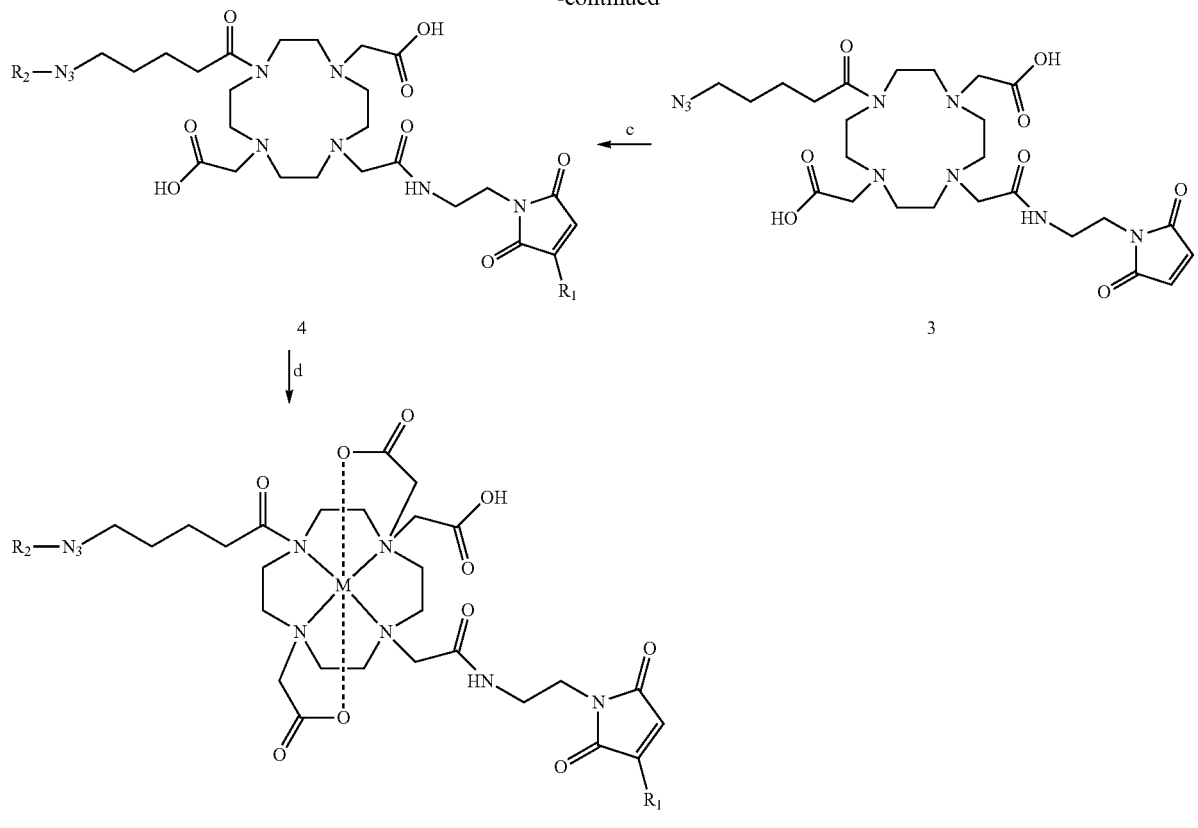

(a) N-(2-aminoethyl)maleimide, DCC, DMAP, CH$_2$Cl$_2$, rt, overnight; (b) TFA/CH$_2$Cl$_2$(1:1), rt, 2 h; (c) antibody, DBCO-IRDye 800, 0.1M phosphate buffer pH 7.2, rt, 7 h; (e) $^{64}$CuCl$_2$, 0.1N NaOAc, pH 6, 37° C., 1 h; M = $^{64}$Cu.

Synthesis of $^{64}$Cu-MMC-Click-(NIR)-mAb7

Compound 1 was synthesized according to Scheme 1 and added to N-(2-aminoethyl)maleimide to produce compound 2. Deprotection of the tert-butyl groups of compound 2 was performed with a TFA/CH$_2$Cl$_2$ mixture at room temperature and resulted in formation of compound 3. Compound 3 was purified by reversed-phase HPLC. Compound 3 is a unique because it can undergo both a regioselective conjugation with a strained cyclooctyne compound and conjugation with thiol-containing compound. Compound 4 was synthesized in a one-pot reaction by first adding an antibody (R1) in phosphate buffer at room temperature for 4 hours, and by then adding DBCO-IRDye 800 (R2) and reacting for an additional 3 hours at room temperature. Compound 4 was purified with a size exclusion desalting column with 7 kDa molecular weight cutoff. MMC-immunoconjugates synthesized by click chemistry schemes yielded 1-3 MMC moieties per antibody.

Figure 11:
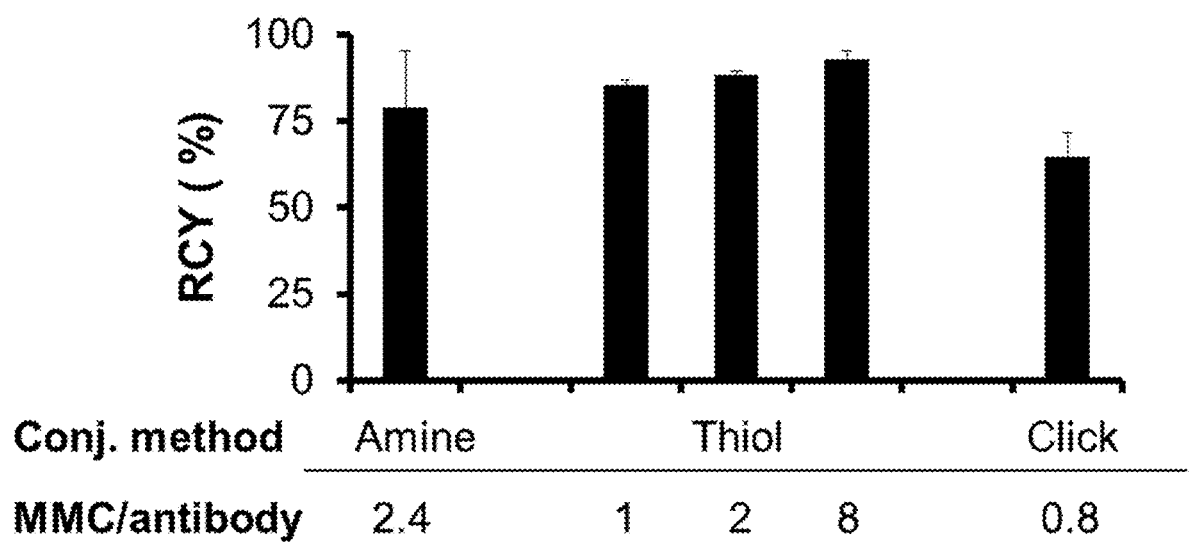
FIG. 11 shows $^{64}$Cu radiolabeling yields with MMC-immunoconjugates produced using amine, thiol, and copper-free click chemistry at varying MMC/antibody ratios.
Figure 12:
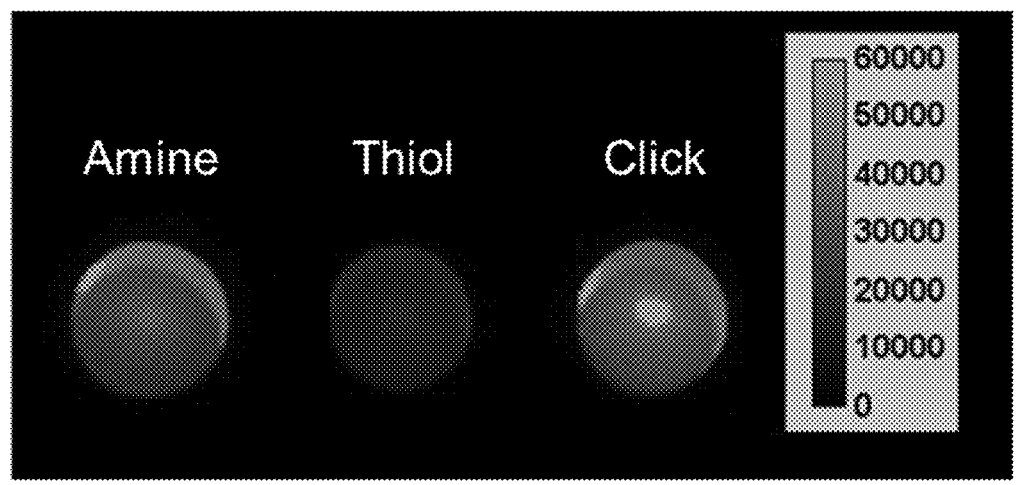
FIG. 12 shows a comparison of fluorescence intensities of MMC-immunoconjugates prepared by different conjugation methods.

Immunoreactivity of the immunoconjugates was retained after MMC conjugation as indicated by ELISA. $^{64}$Cu-labeling was performed as described in example 4 to produce compound 5 with >60% yield and >95% purity (FIG. 11). While the fluorescence intensities of the NHS and sulfhydryl-produced immunoconjugates were reduced following MMC conjugation, the click-based MMC-immunoconjugate demonstrated the highest fluorescent signal suggesting minimal quenching with this approach (FIG. 12).

All of the compounds, compositions, and methods disclosed and claimed herein can be made and executed without undue experimentation in light of the present disclosure. While the compounds, compositions, and methods of this disclosure have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Chen, et al., *Mol Pharm.*, 10:417-427, 2013.
Dearling, et al., *Nucl Med Biol.*, 38:29-38, 2011.
Eisenwiener, et al., *Bioorg. Med. Chem. Lett.*, 10(18):2133-2135, 2000.

Fani, et al., *J Nucl Med.*, 52:1110-1118, 2011.
Ghosh, et al., *Nucl Med Biol.*, 42:177-183, 2015.
Liu, et al., *Chinese J. of Chemistry*, 24(6):785-790, 2006.
Persson, et al., *Nucl Med Biol.*, 41:290-295, 2014.
Pfeifer, et al., *J Nucl Med.*, 53:1207-1215, 2012.
Virgolini, et al., *Eur J Nucl Med Mol Imaging*, 37:2004-2010, 2010.
Zhernosekov, et al., *J. Nucl. Med.*, 48(10): 1741-1748, 2007.

What is claimed:

1. A compound of the formula:

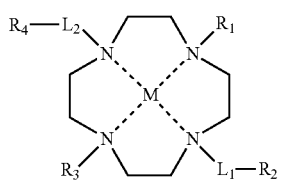
(I)

wherein:
L$_1$ is a covalent bond, —CH$_2$C(O)—, or a thiol reactive group;
L$_2$ is a covalent bond or —CH$_2$C(O)—;
M is a metal atom of any oxidation state or absent;
R$_1$ and R$_3$ are each independently -A-COR$_5$, wherein:
A is alkanediyl$_{(C \leq 8)}$ or substituted alkanediyl$_{(C \leq 8)}$; and
R$_5$ is hydroxy, alkoxy$_{(C \leq 8)}$, or substituted alkoxy$_{(C \leq 8)}$;
R$_2$ is a cell-targeting moiety, wherein the cell-targeting moiety is a peptide or an antibody; and
R$_4$ is a fluorophore group or a chemotherapeutic group, wherein the fluorophore group emits light from about 675 nm to about 2500 nm;
or a pharmaceutically acceptable salt thereof.

2. The compound of claim 1, wherein R$_1$ and R$_3$ are both -A-COR$_5$, wherein: A is alkanediyl$_{(C \leq 8)}$ or substituted alkanediyl$_{(C \leq 8)}$; and R$_5$ is hydroxy, alkoxy$_{(C \leq 8)}$, or substituted alkoxy$_{(C \leq 8)}$.

3. The compound of claim 2, wherein A is alkanediyl$_{(C \leq 8)}$.

4. The compound of claim 3, wherein A is —CH$_2$—.

5. The compound of claim 1, wherein the cell-targeting moiety is a peptide.

6. The compound of claim 5, wherein the peptide comprises from 2 to 100 amino acids.

7. The compound of claim 6, wherein the peptide is of the formula:

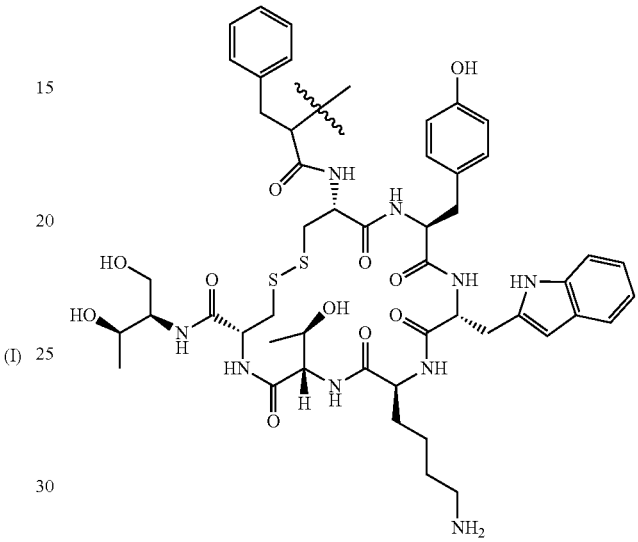

8. The compounds of claim 1, wherein the cell-targeting moiety targets PSMA.

9. The compound of claim 1, wherein the cell-targeting moiety is an antibody.

10. The compound of claim 9, wherein the antibody targets CD20, CD22, CD30, CD52, HER2, VEGF, VEGFR2, EGFR, PD-1, PD-L1, EpCAM, AR, or PSMA.

11. The compound of claim 1, wherein the chemotherapeutic group is selected from a nucleoside analog, an alkylating agent, a topoisomerase inhibitor, a mitotic inhibitor, duocarmycin or duocarmycin analogs, maitansine or maitansine analogs, dolostatin or dolostatin analogs.

12. The compound of claim 1, wherein the fluorophore group further comprises a linker which joins the fluorophore to formula I, further wherein the linker comprises a triazole group.

13. The compound of claim 1, wherein M is a transition metal atom radionuclide.

14. The compound of claim 1, wherein M is a transition metal atom radionuclide, further wherein the radionuclide is $^{45}$Ti, $^{59}$Fe, $^{60}$Cu, $^{61}$Cu, $^{62}$Cu, $^{64}$Cu, $^{67}$Cu, $^{67}$Ga, $^{68}$Ga, $^{89}$Sr, $^{90}$Y, $^{94m}$Tc, $^{99m}$Tc, $^{111}$In, $^{149}$Pm, $^{153}$Gd, $^{153}$Sm, $^{166}$Ho, $^{177}$Lu, $^{186}$Re, $^{188}$Re, $^{211}$At, $^{212}$Bi, or $^{225}$AC.

15. The compound of claim 14, wherein the radionuclide is $^{64}$Cu or $^{68}$Ga.

16. The compound of claim 15, wherein the radionuclide is $^{64}$Cu.

17. The compound of claim 15, wherein the radionuclide is $^{68}$Ga.

18. The compound of claim 1 further defined as:
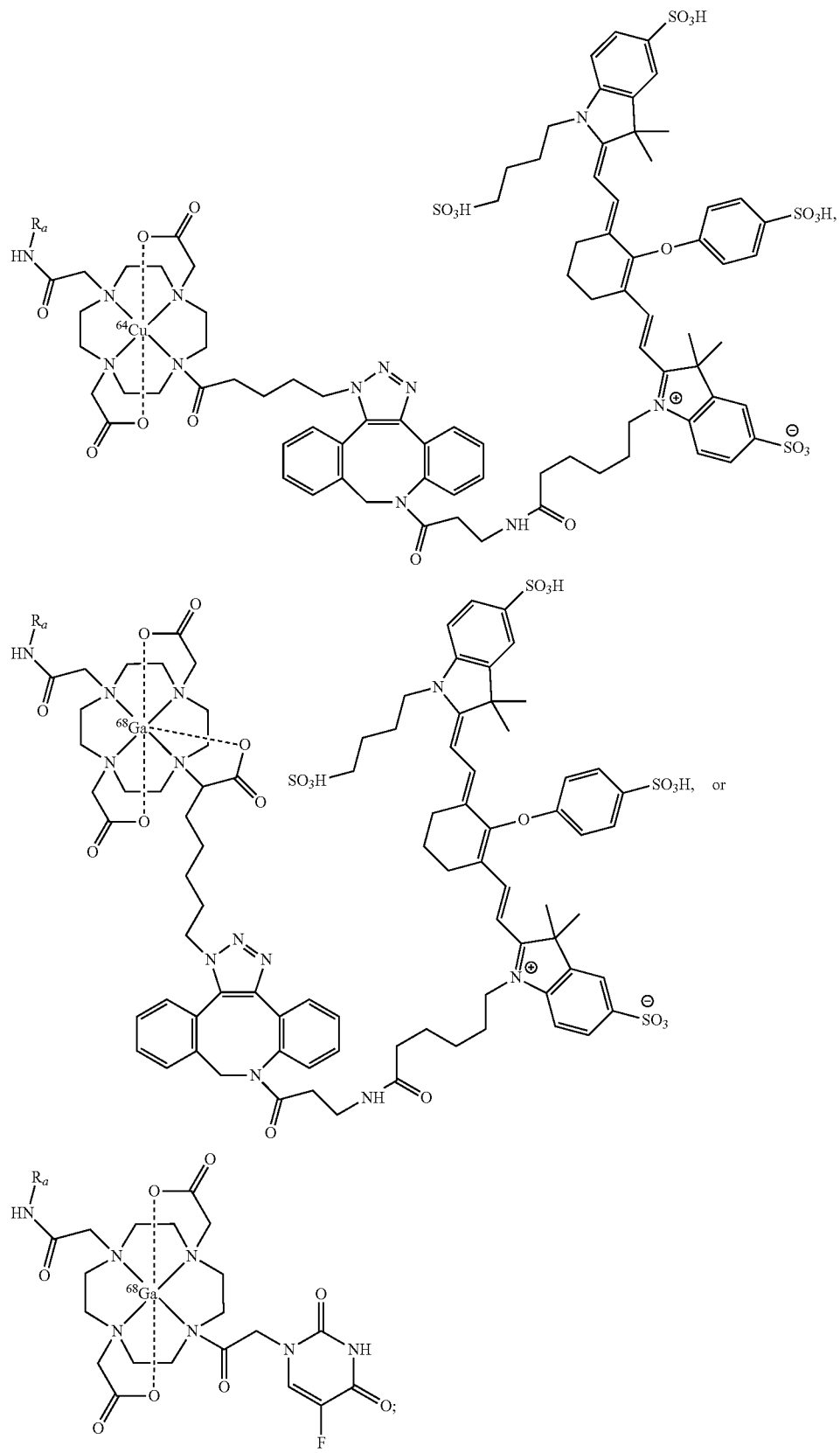

wherein:
R_a is a peptide comprising from 2 amino acids to 100 amino acids;
or a pharmaceutically acceptable salt thereof.
19. The compound of claim 18, wherein the peptide is of the formula:
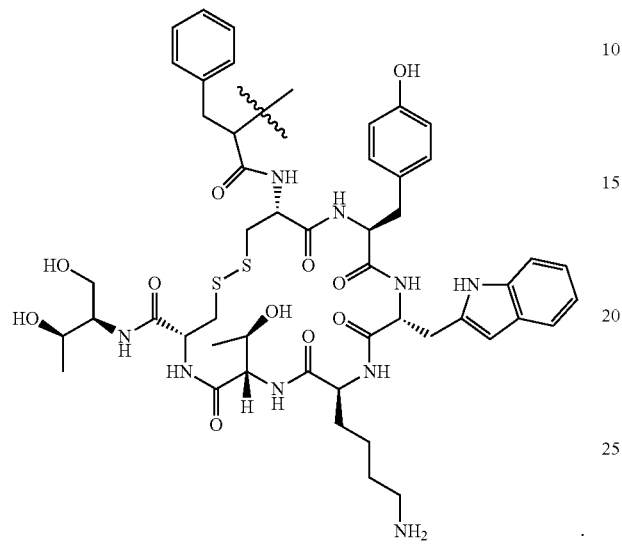
* * * * *

UNITED STATES PATENT AND TRADEMARK OFFICE
CERTIFICATE OF CORRECTION

| | |
|---|---|
| PATENT NO. | : 11,191,778 B2 |
| APPLICATION NO. | : 16/523044 |
| DATED | : December 7, 2021 |
| INVENTOR(S) | : Ali Azhdarinia et al. |

It is certified that error appears in the above-identified patent and that said Letters Patent is hereby corrected as shown below:

In the Specification

Column 1, Lines 9-12, delete the paragraph and insert:
--STATEMENT REGARDING FEDERALLY SPONSORED RESEARCH OR DEVELOPMENT
This invention was made with government support under CA136404 awarded by the National Institutes of Health. The government has certain rights in the invention.-- therefor.

Signed and Sealed this
Thirtieth Day of May, 2023

Katherine Kelly Vidal
*Director of the United States Patent and Trademark Office*